United States Patent
Maddess et al.

(10) Patent No.: US 8,807,753 B2
(45) Date of Patent: Aug. 19, 2014

(54) PUPILLARY ASSESSMENT METHOD AND APPARATUS

(75) Inventors: Teddy Lee Maddess, Lyneham (AU); Andrew Charles James, Kingston (AU)

(73) Assignee: The Australian National University, Australian Capital Territory (AU)

( * ) Notice: Subject to any disclaimer, the term of this patent is extended or adjusted under 35 U.S.C. 154(b) by 486 days.

(21) Appl. No.: 13/132,555

(22) PCT Filed: Dec. 4, 2009

(86) PCT No.: PCT/AU2009/001560
§ 371 (c)(1),
(2), (4) Date: Aug. 23, 2011

(87) PCT Pub. No.: WO2010/063064
PCT Pub. Date: Jun. 10, 2010

(65) Prior Publication Data
US 2011/0292342 A1    Dec. 1, 2011

(30) Foreign Application Priority Data
Dec. 5, 2008 (AU) ............................... 2008906314

(51) Int. Cl.
*A61B 3/14* (2006.01)
(52) U.S. Cl.
USPC .......................................... 351/209; 351/246
(58) Field of Classification Search
USPC .......... 351/209, 205, 246; 600/544, 546, 558, 600/559
See application file for complete search history.

(56) References Cited

U.S. PATENT DOCUMENTS

| | | | |
|---|---|---|---|
| 4,846,567 A | 7/1989 | Sutter | |
| 5,539,482 A | 7/1996 | James et al. | |
| 6,315,414 B1 | 11/2001 | Maddess et al. | |
| 6,702,757 B2 | 3/2004 | Fukushima et al. | |
| 7,006,863 B2 * | 2/2006 | Maddess et al. | ............... 600/544 |

(Continued)

FOREIGN PATENT DOCUMENTS

EP    09829879.7    11/2012

OTHER PUBLICATIONS

Kolic, M. et al, "Attempting balanced multifocal pupilographic perimetry" (Poster presentation) ARVO 2009 Annual meeting, Ft. Lauderdale, FL, May 3-7, 2009.

(Continued)

*Primary Examiner* — Hung Dang
(74) *Attorney, Agent, or Firm* — Wood, Phillips, Katz, Clark & Mortimer

(57) ABSTRACT

A system and method for assessing the function of parts of the nervous system of a subject by measuring the pupillary responses to at least one stimulus ensemble comprising a plurality of individual stimuli; the method comprising: presenting a sequence of selected individual stimuli from the at least one stimulus ensemble to the nervous system of a subject thereby evoking pupillary responses in at least one pupil of the subject, selected individual stimuli being concurrently presented in the sequence, wherein the individual stimuli are each individually balanced such that the pupillary responses evoked by individual stimuli in the ensemble are balanced according to the strength of the neural responses evoked by the individual stimuli; detecting responses of the pupil or pupils evoked by the stimuli using a sensor; and processing the detected responses to relate them to the function of the subject's neural responses to some or all of the individual stimuli of the ensemble.

35 Claims, 19 Drawing Sheets

(56) References Cited

U.S. PATENT DOCUMENTS

| | | |
|---|---|---|
| 7,334,895 B2 | 2/2008 | Kandel et al. |
| 7,377,646 B2 | 5/2008 | Suzuki |
| 2003/0163060 A1* | 8/2003 | Maddess et al. ............ 600/544 |
| 2008/0108908 A1 | 5/2008 | Maddess et al. |
| 2010/0249532 A1 | 9/2010 | Maddess et al. |

OTHER PUBLICATIONS

Maddess et al, "Balanced liminance multifocal pupillographic perimetry" (Poster presentation) ARVO 2009 Annual meeting, Ft. Lauderdale, FL May 3-7, 2009.

Maddess et al, "Multifocal pupillographic visual field testing in glaucoma", Clinical and Experimental Opthalmology 2009, 37 pages 678-369.

White, GL, et al, "Pupillary activity while listening to verbal passages", Journal of Research in Personality, 1978, vol. 12, Issue 3, pp. 361-369.

Wilhelm, H. et al, "Pupil perimetry using M-sequence simulation technique", Investigative Opthalmology and Visual Science, Apr. 2000, vol. 41, No. 5, pp. 1229-1239.

Lei Tan et al, "Multifocal pupillary light response fields in normal subjects and patients with visual field defects", Vision Research, vol. 41, No. 8, Apr. 1, 2001, p. 107.

Hong et al, "Comparison of . . . & visual perimetry in normal eyes: decibel . . . ", investigative Opthalmology & Visual Science, US vol. 42, No. 5, 1 Apr. 1, 2001, p. 957-65.

Japanese Office Action dated Nov. 19, 2013 (Japanese language) on Japanese Patent Appln. No. 2011-538796 & English translation of same.

Japanese Patent Publication No. JP 2007-512050 A (counterpart of US Patent Appln. Pub. No. US 2008108908; U.S. Patent No. 8583223 ).

Japanese Patent Pub. No. JP 2002-253509 A (counterpart of US Patent Appln. Pub. No. US 2002099305; US Patent No. 6702757).

Japanese Patent Publication No. JP 2003-527913 A (counterpart of US Patent Appln. Publication No. US 2003163060; US Patent No. 7006863.

Japanese Patent Publication No. JP 2005-342107 A (counterpart of US Patent Application Publication No. US 2005280776; (US Patent No. 7377646.

P.D. Gamlin, "The pretectum: connections and oculomotor-related roles", Prog Brain Res, vol. 151, 2006, pp. 379-405.

D.M. Dacey et al., "Melanopsin-expressing ganglion cells in primate retina signal colour and irradiance and project to the LGN", Nature, vol. 433, Feb. 17, 2005, pp. 749-754.

S. Shipp, "The functional logic of cortico-pulvinar connections", Philos Trans R Soc Land B Biol Sci, vol. 358, Apr. 4, 2003, pp. 1605-1624.

S. Clarke et al., "Thalamic projections of the fusiform gyrus in man", Eur J. Neurosci, vol. 11, No. 5, May 1999, pp. 1835-1838.

F. J. Rucker and P. B. Kruger, "Accommodation responses to stimuli in cone contrast space", Vision Res, vol. 44, 2004, pp. 2931-2944.

J. Slooter and D. van Norren, "Visual acuity measured with pupil responses to checkerboard stimuli", Invest Ophthalmol Vis Sci, vol. 19, No. 1, 1980, pp. 105-108.

K.D. Cocker and M.J. Moseley, "Development of pupillary responses to grating stimuli", Ophthalmic Physiol Opt, vol. 16, No. 1, Jan. 1996, pp. 64-67.

E.A. Bernardete et al., "Contrast gain control in the primate retina: P cells are not X-like, some M cells are", Vis Neurosci, vol. 8, 1992, pp. 483-486.

Tomoda A et al., "Spectroscopic studies of brunescent cataractous lenses", FEBS Lett. Jul. 27, 1987; 219(2):472-6.

* cited by examiner

PUPILLARY ASSESSMENT METHOD AND APPARATUS

TECHNICAL FIELD

The present invention relates to assessment of the function of the nervous system using the pupil and its special properties. A particular use of the pupil is as a means to assess the operation of the visual sensory system.

The invention has been developed primarily for use as a method and apparatus for improved assessment and quantification of the visual fields field of human and animal subjects, and will be described hereinafter with reference to this application. However, it will be appreciated that the invention is not limited to this particular field of use. In particular, the methods and apparatus described herein may also be applicable for assessment of visual accommodation, visual acuity, hearing and audio-visual function, emotional state, drug use and mental health disorders.

BACKGROUND

Any discussion of the background art throughout the specification should in no way be considered as an admission that such background art is prior art, nor that such background art is widely known or forms part of the common general knowledge in the field.

The pupils of the eye are often thought to only serve the function of a camera aperture, regulating the flux of light into the eye via a simple reflex mediated by parts of the mid-brain. In fact recent studies have shown that the input to the pupil system from the visual nervous system is much more complex than previously thought. This complexity is derived from the inputs from various brain areas that contribute to the pupillary response. The major site of pooling (i.e. the combination of many component signals to give a single observed response) of brain signals that contribute to the pupillary response is the pretectal olivary nucleus (PON). The two PONs then convey that information to both of the Edinger-Westphal (EW) nuclei on the two sides of the brain which in turn innervate the pupils via the oculomotor nerves. This means that each pupil receives information about the pooled activity of both retinas. Thus each pupil can independently provide information on the operation of both retinas. When a pupil gives a response to the retina of its own eye this is said to be a direct response. When a pupil responds to activity from the retina of its fellow eye that is said to be a consensual response.

About half the input to the PON is from melanopsin containing retinal ganglion cells (mcRGC) that come directly from the eye [for further information see P. D. Gamlin, "The pretectum: connections and oculomotor-related roles", Prog Brain Res, Volume 151, Pages 379-405]. The nerve fibres of these and all the other types of retinal ganglion cells make up the optic nerve. The mcRGCs have two separate types of responses to light [for further information see D. M. Dacey, H. W. Liao, B. B. Peterson, F. R. Robinson, V. C. Smith, J. Pokorny, K. W. Yau and P. D. Gamlin, "Melanopsin-expressing ganglion cells in primate retina signal colour and irradiance and project to the LGN", Nature, Volume 433, Pages 749-754]. The first response type derives from melanopsin that is present in the retinal bodies of these ganglion cells. Unlike the light responses of the photoreceptor cells of the retina the melanopsin driven response of mcRGCs has no light adaptation mechanism and so increases steadily with increasing light level. The melanopsin pigment responds to blue light and the response itself is very slow, taking several seconds to respond to a transient increase in blue light. This slow integrative response is mainly responsible for the mean pupil size, small in the bright light, more dilated in darkness.

As with all other types of retinal ganglion cells (RGCs) the mcRGCs also convey signals derived from rod and cone photoreceptor cells of the eye. The cone driven component responds positively to yellow light (luminance) and negatively to blue light. This response type is often referred to as a Yellow-ON/Blue-OFF class of response. These responses are much more transient following the time resolution of the cones. This system also necessarily embodies the light adaptation mechanism possessed by the photoreceptors and cells that process photoreceptor information such as bipolar and horizontal cells before those signals are passed to the RGCs. Other types of retinal ganglion cells convey information to the brain about differential red and green content of images, and also the luminance (brightness) information in images. The main luminance signals are conveyed to the brain by parasol ganglion cells. The red-green colour signal is carried by midget ganglion cells. Together the parasol and midget cells make up the majority of the optic nerve fibres.

Most types of retinal ganglion cells, including parasol and midget cells, and also about half of the mcRGCs, proceed to the visual cortex via the lateral geniculate nucleus (LGN). The visual cortex is a massively interconnected set of visual processing areas. Many of these visual cortical areas are also multiply and reciprocally connected to the midbrain via the pulvinar areas [for further information see S. Shipp, "The functional logic of cortico-pulvinar connections", Philos Trans R Soc Lond B Biol Sci, Volume 358, Pages 1605-1624; and S. Clarke, S. Riahi-Arya, E. Tardif, A. C. Eskenasy and A. Probst, "Thalamic projections of the fusiform gyrus in man", Eur J Neurosci, Volume 11, Pages 1835-1838].

Higher centres within the extrastriate visual cortex then communicate with the PON providing about half its input nerve supply [refer to P. D. Gamlin, referenced above]. Among the various signals computed in the cortex is distance information derived from the binocular disparity between the eyes.

Another function of the pupils is the accommodative reflex by which the pupils become small when persons view objects that are close to them. Presumably this aids near vision by increasing the depth of field. Obviously the accommodative response requires information about depth and is provided to the PON by its binocular cortical inputs. The accommodative response is known to contain input from the luminance and red-green differential input systems mentioned above [for further information see F. J. Rucker and P. B. Kruger, "Accommodation responses to stimuli in cone contrast space", Vision Res, Volume 44, Pages 2931-2944]. The spectral colour sensitivity of the human luminance system is provided by the sum of red and green sensitive cone inputs, leaving the net peak spectral sensitivity corresponding to yellow hues.

Another input to the pupil that likely derives from the visual cortex are the pupillary responses to achromatic, equiluminant, high spatial frequency patterns, which permit visual acuity to be assessed via the pupillary responses, even in children [see J. Slooter and D. van Norren, "Visual acuity measured with pupil responses to checkerboard stimuli", Invest Ophthalmol Vis Sci, Volume 19, Pages 105-8; or K. D. Cocker and M. J. Moseley, "Development of pupillary responses to grating stimuli", Ophthalmic Physiol Opt, Volume 16, Pages 64-67].

Therefore, the pupil has at least two possible sources of sensitivity to yellow luminance stimuli: the Yellow-ON response component of the mcRGCs and the parasol cells, the main constituents of the projection to the magnocellular layers of the LGN. The parasol RGCs have a gain control mechanism that makes them preferentially responsive to low spatial frequencies and high temporal frequencies [see E. A. Benardete, E. Kaplan and B. W. Knight, "Contrast gain control in the primate retina: P cells are not X-like, some M cells are", Vis Neurosci, Volume 8, Pages 483-486]. The yellow-ON component of the mcRGCs does not seem to have such a gain control mechanism.

Overall, the diverse nerve supply to the pupil means that potentially it can report on the activity of a large proportion of the optic nerve fibres, and various parts of the visual thalamus and cortex. One common form of visual testing done on human subjects is characterising the extent and function of the visual fields of the eyes.

Human visual fields are commonly assessed by static perimetry. The basic form of this assessment involves sequentially presenting small test stimuli to each of a preset ensemble of locations across the visual field. During the test subjects indicate subjectively whether or not they have seen each test stimulus that they have been presented with whilst they maintain their gaze on a fixation target for the duration of the test. For most perimeters, subjects provide behavioural responses, such as button presses, to indicate when they have seen a particular test stimulus. Component parts of the visual field can have characteristic visual abilities. The goal of perimetry is thus to assess the visual ability or abilities of each part of the measured portion of the visual field.

Unrelated technologies are used to assess properties of the pupils of the eye, for example, devices that measure the static size of the pupil under particular viewing conditions are referred to as pupillometers and devices that monitor the changing size of pupils of time are referred to as pupillographs, and the distinctions between such devices are outlined by the USA Food and Drug Administration. Pupillographs have previously been used in conjunction with standard perimetry stimuli to measure responses to those stimuli and provide perimetric maps of the visual fields, however, these systems have proved to be unreliable and have not achieved commercial form or acceptance.

There are many reasons to assess the visual fields. For example the visual fields are fundamentally limited by physical features of the face such as the nose, brow ridges, and cheek bones, which change during development. Therefore, assessing the visual fields can be useful for tracking facial development or examining if a normal person's facial features provide them with a suitable visual field, for example, for use in certain sports or occupations. The visual nervous system continues to develop until adulthood and this can affect aspects of the visual field. Therefore, visual field testing can be used to determine the state of a young person's development. Physiological stress testing can also reversibly alter the visual fields. Therefore, the availability of a rapid means to test the visual fields before during and after the stress test is beneficial for stress level assessment. Visual field testing can also be useful in the management of disease rather than assisting in diagnosis per se. For example, persons with diseases such as multiple sclerosis can have periodic losses of vision due to transient conditions such as optic neuritis. The optic neuritis often resolves quickly but this can be aided by treatment. Visual field testing can therefore be used to assist in the management of such problems.

Similarly other diseases, such as glaucoma, can cause localised damage to smaller areas of the visual field. Again these diseases are amenable to current, and presumably future, treatments so visual field testing is useful to determine the effectiveness of treatment over time. Of course, this means visual field testing can be useful in providing data that would assist a physician, in conjunction with other data, to make a diagnosis of a disease such as glaucoma or other disease which affects the visual function of the subject. In the case of glaucoma, other data that would assist to confirm glaucoma, once a visual field defect had been observed with field testing, would include: eye pressure tests, measurement of the thickness of the nerve fibre layer of the retina by means of polarimetry or optical coherence tomography (OCT), and or the topography of the head of the optic nerve, often called the optic disc, by visual inspection, stereo fundus photography, OCT or confocal microscopy. These would normally be performed in conjunction with other tests such as magnetic resonance imaging, positron emission spectroscopy of the brain or electroencephalography, to eliminate brain related sources of the visual field defect such as stroke.

The primary drawback with existing static perimeter systems, however, is the subjective nature of the testing which causes the tests to suffer from inaccuracies and human/patient error since the current tests rely on the patient's ability to respond behaviourally to their detection of a stimulus (static perimeters do not use pupillary responses). Typically, the patient has a limited window of time in which to respond to the stimulus, and is presented with a limited number of stimuli. Therefore, if the patient is not concentrating some false positive or false negative responses will be delivered and the perimetry device will not be able to establish visual sensitivity well, thus compromising the accuracy of the diagnosis. The test may also be compromised by the patient's inability, or lack of desire as in cases of malingering, to respond to the stimulus accurately which may be caused by any number of variables for example whether the patient suffers from autism, age-related disorders, and drug impairment or intoxication to name a few.

A further disadvantage of current tests is the time in which a test may be completed. Since the patient must respond subjectively to each stimulus, this places a limit on the time in which the test may be conducted.

An objective alternate method for mapping the visual fields is to employ so-called multifocal methods. In these methods one uses an ensemble of visual stimuli, each member of the ensemble being presented to a particular sub-region of the visual field. The appearance or non-appearance of stimuli at each sub-region of the visual field is modulated by aperiodic pseudorandom temporal sequences that are mutually statistically independent. Optimally the modulation sequences should be completely statistically independent, that is the modulation sequences should be mutually orthogonal, which is to say having zero mutual correlation. A variety of patents related to various orthogonal (U.S. Pat. No. 5,539,482 to Maddess & James, the disclosure of which is wholly incorporated herein by cross-reference) and near orthogonal sequences (for example U.S. Pat. No. 4,846,567 to Sutter) exist, but recent analysis methods permit more general stimuli to be used (for example U.S. Pat. No. 6,315,414, U.S. Pat. No. 7,006,863 and International Patent Publication No. WO 2005/051193, all to Maddess & James, the disclosures of which are wholly incorporated herein by cross-reference).

The basic idea of multifocal methods is that the temporal statistical independence of the stimuli permits many stimuli to be presented concurrently, for example at different locations in the visual field, or different stimulus conditions, each driven by its own sequence. Then the estimated responses to presentations at all the test locations, or stimulus conditions, may be recovered from recordings of neural activity of the visual nervous system. The neural responses to the stimuli can be recorded by electrical or magnetic detectors, changes to the absorption, scattering or polarization infrared light or other electromagnetic radiation from parts of the nervous system, or functional magnetic resonance imaging. As can be appreciated, sensors for detection of such neural responses are complex and rely on correct placement for efficient operation, typically on the scalp of the patient. Also, methods such as electroencephalography suffer from the fact that different subjects have different brain anatomy and this affects the signals measured on the scalp. Subjects are also often averse to the placement of electrodes on their scalp or eyes, and there are health risks associated with any such contact method. Responses to the stimuli may be detected through monitoring of the pupils, which have the advantage of permitting non-contact assessment, however to date there are no commercial perimetry systems that use pupillography.

Accordingly, there is a need for a rapid objective, non-contact visual field assessment, which can be used for a variety of purposes, not just the assessment of the visual field of a subject, for example visual accommodation, visual acuity, hearing and audio-visual function, emotional state, drug use and mental health.

It is an object of the present invention therefore to substantially overcome or at least ameliorate one or more of the disadvantages of the prior art, or at least to provide a useful alternative, particularly when it is desirable to test an ensemble of stimuli (eg, visual, auditory or other stimulus detectable via a pupillary response) concurrently.

SUMMARY

As mentioned above the pupils are an excellent substrate for recording neural responses of the visual nervous system. Additionally the pupils are known to provide information about the mental illness and emotional states, response to auditory stimuli, audio-visual interactions, visual acuity, and the visual distance accommodation system. The inventors have surprisingly discovered that the pupillary system has special properties described herein that can be harnessed to provide more reliable responses from parts of the visual field, or component parts of other stimuli, such as accommodative stimuli, or stimuli that evoke particular emotions, as measured from responses to those stimuli.

Secondarily, the method is designed to enhance the responses of the pupils to aid in other assessments of the visual system that can employ one or both pupils in human or animal subjects. This method and apparatus or systems for implementation of the method as described herein would be of use when the pupils are used to assess any collection of these functions or collections of visual stimuli, allowing the pupillary responses to desired subsets of functions and stimuli to be enhanced relative to the others in the total set being tested.

According to a first aspect, there is provided a method for assessing the nervous system of a subject. The method may comprise the step of presenting a sequence of selected individual stimuli from at least one stimulus ensemble to the nervous system of a subject. The sequence of selected individual stimuli may be adapted to evoke pupillary responses in at least one pupil of the subject. The stimulus ensemble may comprise a plurality of individual stimuli. Selected individual stimuli may be concurrently presented in the sequence. The individual stimuli may each be individually balanced. The individual stimuli may each be individually balanced such that the pupillary responses evoked by individual stimuli in the ensemble are balanced according to the strength of the neural responses evoked by the individual stimuli. The method may further comprise the step of detecting using a sensor responses of at least one pupil evoked by the stimuli.

The method may further comprise the step of relating the detected pupillary responses to the function of the subject's neural responses to at least two of the individual stimuli of the ensemble.

According to an exemplary arrangement of the first aspect, there is provided a method for assessing the nervous system of a subject, the method comprising the steps of: presenting a sequence of selected individual stimuli from at least one stimulus ensemble to the nervous system of a subject adapted to evoke pupillary responses in at least one pupil of the subject, said stimulus ensemble comprising a plurality of individual stimuli, selected individual stimuli being concurrently presented in the sequence, the individual stimuli each being individually balanced such that the pupillary responses evoked to each of the individual stimuli in the ensemble are balanced according to the strength of the neural responses evoked by the individual stimuli; detecting using a sensor responses of at least one pupil evoked by the stimuli; and relating the detected pupillary responses to the function of the subject's neural responses to at least two of the individual stimuli of the ensemble The individual stimuli may each be individually balanced such that responses of the pupils to more effective stimuli in the ensemble are reduced and thereby producing larger responses of the pupils to less effective stimuli. The relationship between stimulus intensity and pupillary response size may be described by nonlinear functions. The nonlinear functions may define stimulus weights for balancing the pupillary response. The nonlinear functions may define stimulus weights for balancing the pupillary response to each of the individual stimuli. Different nonlinear functions may be used for each individual stimulus in the ensemble. The nonlinear stimulus/response function may be a power function of the form Response=K×stimulus$^z$.

The method may further comprise the step of obtaining attenuating weights for each of the stimuli in the ensemble. The attenuating weights may be logarithmic. The weights may be obtained by expressing the responses sizes of the stimuli in the ensemble in logarithmic form to provide linear balancing weights. The linear balancing weights may be raised to the power z. Each individual stimulus in the ensemble may be associated with a unique exponent for expression of the attenuating weight for each stimulus.

The stimuli may be visual stimuli. The visual stimuli may be presented to a subject at multiple locations in the subject's visual field concurrently. The visual stimuli may be presented to a subject at multiple locations in the visual field of one or both of the subject's eyes. The resulting set of pupillary responses evoked by each of the visual stimuli may provide a map of visual function across the visual field of the one or both eyes. The visual stimuli may thus be monocular or binocular presented separately or concurrently. The stimuli may be presented aperiodically, each controlled by different sequences that are statistically independent, each with selected mean inter-stimulus symbol interval periods. The mean inter-stimulus interval period may be selected to be either about 1 s/region or about 4 s/region, or more generally between about 0.25 and about 16 s/region.

The ensemble of visual stimuli may thus be an ensemble of multifocal stimuli. In a sequence of selected individual stimuli of the multifocal stimuli ensemble, the appearance or non-appearance of individual stimuli in the ensemble or other modulations of the stimuli such as intensity, colour (hue) or spatial frequency may be controlled by statistically independent sequences.

Selected individual stimuli of the ensemble may be associated with a weighting function wherein the luminance of the selected stimuli is controlled such that regions of the visual field in which unweighted stimuli evoke large neural responses is decreased.

The visual stimuli at one or several locations may alternate between one of a number of stimulus conditions. The stimulus conditions may be selected from the group consisting of stimulus luminance level, stimulus colour or hue. The stimulus conditions for each stimulus in the ensemble may each be controlled by a unique statistically independent sequence such that the pupillary responses are representative of the neural responses affected by a stimulus space spanned by those stimulus conditions.

The ensemble of visual stimuli may be presented as an ensemble of grating or checkerboard stimuli. The grating or checkerboard stimuli may be dominated by a range of different spatial frequencies for determination of the visual acuity or spatial frequency tuning of the tested portion of a subject's visual field.

The ensemble of stimuli may be presented at one or a plurality of spatially resolved locations in the visual field of the subject. The pupillary responses to the spatially resolved stimuli may be representative of the neural responses to the concurrently presented spatial frequencies thereby to obtain information about the visual acuity and spatial frequency sensitivity of the subject.

The visual stimuli may be adapted to provide a measure of the distance to objects in the visual field. The measure of the distance to objects in the visual field may be determined by presenting stereo disparity cues to each of the subject's eyes, such that the pupillary responses are representative of the function of the accommodative system of the subject's eyes.

The stimuli in the ensemble may be adapted such that the pupillary responses evoked by said stimuli are substantially unsaturated.

The ensemble of visual stimuli may be a first ensemble for presentation to one eye of the subject. The method may further comprise the step of concurrently presenting a second ensemble of unique visual stimuli to the other eye of the subject. The method may further comprise the step of recording the pupillary responses of a selected one of the two retinas. The method may further comprise the step of characterising the pupillary response of the retina associated with the recorded pupil by the direct pupil response. The method may further comprise the step of and characterising the pupillary response of the other retina by the consensual response of the recorded pupil.

In an exemplary arrangement, the method may further comprise the steps of: concurrently presenting a second ensemble of unique visual stimuli to the other eye of the subject; recording the pupillary responses of a selected one of the two retinas; characterising the pupillary response of the retina associated with the recorded pupil by the direct pupil response; and characterising the pupillary response of the other retina by the consensual response of the recorded pupil.

The ensemble of stimuli may be an ensemble of auditory stimuli. The ensemble of stimuli may evoke particular emotions, or modulate the mental health of a subject. The method may further comprise the step of recording the pupillary response of the subjected evoked by the ensemble of stimuli. The method may further comprise the step of characterising the function of those neural mediated emotional or mental health mechanisms of the subject from the recorded responses. In an exemplary arrangement, the method may further comprise the steps of recording the pupillary response of the subjected evoked by the ensemble of stimuli; and characterising the function of those neural mediated emotional or mental health mechanisms of the subject from the recorded responses.

The ensemble of stimuli may be an ensemble of different drugs or other chemical substances, or difference dosages of a drug or substance, that are known to affect the function of the pupils. The ensemble of stimuli may comprise a mixture of visual, accommodative, auditory, emotional, or chemical stimuli.

According to a second aspect, there is provided a system for assessing the nervous system of a subject. The system may comprise means for generating sequences of stimuli. The means may be a computer system. The sequences of stimuli may be selected or derived from at least one stimulus ensemble. The sequences may be adapted to evoke pupillary responses in at least one pupil of the subject. The stimulus ensemble may comprise a plurality of individual stimuli. The stimulus generation means may individually select, determine or associate at least one weighting function for each of the individual stimuli in the stimulus ensemble. The one weighting function for each of the individual stimuli in the stimulus ensemble may be selected, determined or associated such that the pupillary responses to individual stimuli in the ensemble are balanced. The pupillary responses to individual stimuli in the ensemble may be balanced according to the strength of the neural responses evoked by the individual stimuli. The system may further comprise a display means for presenting said sequence of balanced stimuli to the nervous system of a subject for the generation of pupillary responses in at least one pupil of the subject. The system may further comprise a sensor for detecting the pupillary responses of at least one pupil evoked by the sequence of balanced stimuli. The system may further comprise a processor for recording and relating the detected pupillary responses to relate them to the function of the subject's neural responses to at least two of the individual stimuli of the ensemble.

According to an exemplary arrangement of the second aspect, there is provided a system for assessing the nervous system of a subject, the system comprising: means for generating sequences of stimuli from at least one stimulus ensemble adapted to evoke pupillary responses in at least one pupil of the subject, said stimulus ensemble comprising a plurality of individual stimuli, the stimulus generation means individually determining at least one weighting function for each of the individual stimuli in the stimulus ensemble such that the pupillary responses to individual stimuli in the ensemble are balanced according to the strength of the neural responses evoked by the individual stimuli; display means for presenting said sequence of balanced stimuli to the nervous system of a subject for the generation of pupillary responses in at least one pupil of the subject; a sensor for detecting the pupillary responses of at least one pupil evoked by the sequence of balanced stimuli; and a processor for recording and relating the detected pupillary responses to relate them to the function of the subject's neural responses to at least two of the individual stimuli of the ensemble.

The system may further comprise a database of recorded data, the recorded data comprising information on at least one or more of: the strength or mean strength of the neural responses evoked in at least one subject by the individual stimuli; the strength or mean strength of the pupillary responses evoked in at least one subject by the individual stimuli; wherein the stimulus generation means determines the at least one weighting function for each of the individual stimuli from an analysis of the recorded data. The analysis of the recorded data for determination of the weighting function(s) may provide a relationship between the intensity of the individual stimuli and pupillary responses evoked therefrom in the form of one or more nonlinear functions. The nonlinear stimulus/response function may be a power function of the form Response=K×stimulus$^z$. Each individual stimulus in the ensemble may be associated with a unique exponent for expression of the attenuating weight for each stimulus.

The individual stimuli of the ensemble may be visual stimuli. The visual stimuli may be presented to a subject at multiple locations in the visual field of one or both of the subject's eyes concurrently, such that the resulting set of pupillary responses to each individual stimulus may provide a map of visual function across the visual field of the one or both eyes.

The means for generating sequences of stimuli may be adapted to present the stimuli aperiodically, each stimulus controlled by different sequences that are statistically independent, with selected mean inter-stimulus symbol interval periods. The means for generating sequences of stimuli may be adapted to selectively present the aperiodic stimuli with a mean inter-stimulus interval period of either about 1 s/region or about 4 s/region, or more generally between about 0.25 and about 16 s/region.

According to a further aspect, there is provided an apparatus for the application of the method of the first aspect. According to a still further aspect, there is provided an apparatus for the implementation of the system of the second aspect. According to a further aspect, there is provided an apparatus for implementation of the system of the second aspect with the method of the first aspect.

BRIEF DESCRIPTION OF THE DRAWINGS

Arrangements of the methods, apparatus and systems will now be described, by way of an example only, with reference to the accompanying drawings wherein.

DETAILED DESCRIPTION

Unless defined otherwise, all technical and scientific terms used herein have the same meaning as commonly understood by those of ordinary skill in the art to which the invention belongs. For the purposes of the present invention, the following terms are defined below.

The articles "a" and "an" are used herein to refer to one or to more than one (i.e. to at least one) of the grammatical object of the article. By way of example, "an element" refers to one element or more than one element.

The term "about" is used herein to refer to frequencies or probabilities that vary by as much as 30%, preferably by as much as 20%, and more preferably by as much as 10% to a reference frequency or probability.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Although any methods and materials similar or equivalent to those described herein can be used in the practice or testing of the present invention, preferred methods and materials are described. It will be appreciated that the methods, apparatus and systems described herein may be implemented in a variety of ways and for a variety of purposes. The description here is by way of example only.

Figure 1A:
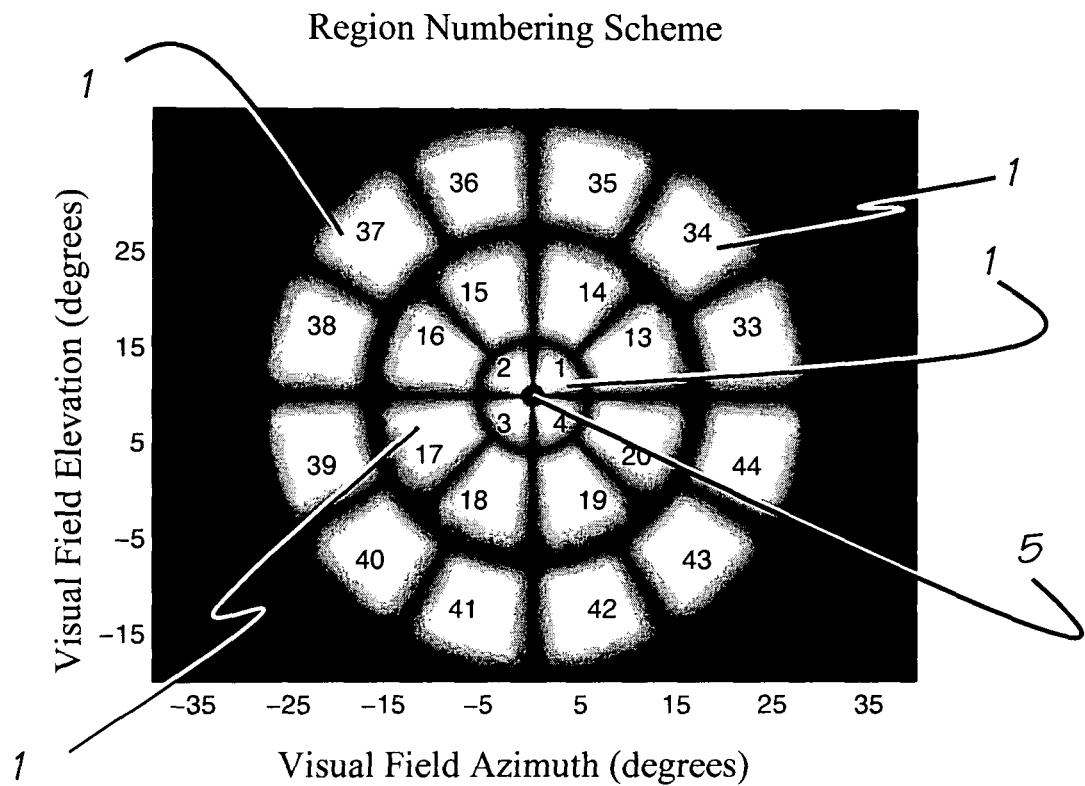
FIGS. 1A and 1B together illustrate two sub-sets of a single ensemble of 44 stimuli that are designed to be presented to an eye while a subject fixates the centre of the ensemble, wherein some of the stimuli would potentially overlap if presented at the same time.
Figure 1B:
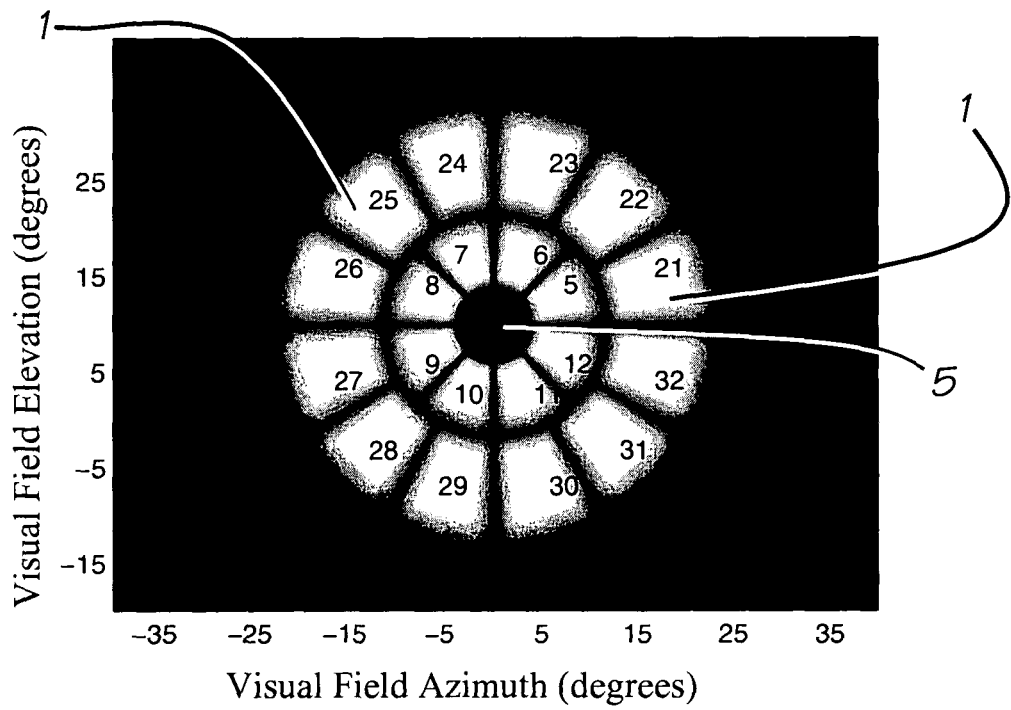

FIGS. 1A and 1B together show two sub-sets of a single ensemble of 44 polar scaled stimuli 1 for visual presentation to a subject. Each of the individual stimuli 1 are presented at selected locations centred at points on a polar sampling grid spanning a portion of the visual field. The individual stimuli, if presented simultaneously at the sampling grid points, may be configured such that they would potentially overlap in some parts of the visual field but with no overlap across the vertical and horizontal meridians of the sampling grid. The overlapping of the stimuli may be such that spatial aliasing of the stimuli on the sampling grid is minimised. That is, the stimuli may transmit little to no spatial frequencies that the sampling grid cannot represent accurately. The stimuli may alternatively or concurrently be configured such that, if presented simultaneously, individual stimuli may be sufficiently overlapping such that they transmit little to no spatial frequencies above the critical sampling frequency of the sampling grid, referred to as the Nyquist rate and defined by the geometry of the sampling grid. The profiles of the stimuli may be smoothly varying and/or blurred. The smoothly varying profiles of the individual stimuli (particularly at the edges and/or corners of the individual stimuli) may be sufficiently smooth such that they comprise only low spatial frequency Fourier components. The profiles of the stimuli may be smoothly varying such that the individual stimuli contain only spatial frequencies that are less than or equal to the highest spatial frequency that can be represented by the sampling grid defined by the points of the sampling grid. The sufficiently smooth or blurred individual stimuli have the significant advantage that the subject may not be well refracted (that is, may have incorrect, insufficient or even no refractive correction) without significantly affecting the results of the assessment of the subject's visual field. These properties of the stimulus sampling grid and the individual stimuli are the subject of International PCT application PCT/AU2008/001663 to Maddess and James, the contents of which are incorporated herein by cross-reference.

The 44 stimulus regions in the array are numbered for reference from 1 to 44 as indicated in FIGS. 1A and 1B. The stimuli are intended to be presented in a desired sequence whilst a subject fixates the centre 5 of the array and thus, when a given stimulus region appears its position in visual space it maps onto a particular part of the retina, thereby establishing a correspondence between the resulting map of visual activity with corresponding parts of the retina and retinotopically mapped parts of the visual brain. Notice that in this particular arrangement, each region has the same maximum, central brightness, and that the array extends to approximately 30 degrees radius from the central fixation point 5. Ordinarily, the stimuli 1 may be each be presented one at a time in a desired sequence as part of a test and a subject being tested may subjectively respond to each stimulus region by a button press or other means.

In the present arrangement, the ensemble is presented in a multifocal stimulus arrangement where the appearance or non-appearance of stimuli in individual regions is controlled by statistically independent aperiodic pseudorandom sequences. Thus, although the regions in which the stimuli can appear within the ensemble can potentially overlap, in practice the presentation of the stimuli may be controlled so that any such overlap of stimuli appearing at the same time occurs rarely or never as desired. Note, however, that the multifocal presentation allows for several stimuli to appear in selected regions at the same time due to the multifocal stimulus sequences being statically independent. In the present example, particular care was taken that near neighbours were rarely stimulated on successive frames of the presentation sequences of stimuli displayed for a test, such that the stimuli conformed to the spatially sparse stimulus arrangement (described in greater detail in International Patent Publication No. WO 2005/051193, to Maddess & James). In principle, multifocal methods can tolerate overlaps between adjacent stimuli, and indeed may benefit by the overlaps by permitting nonlinear interactions to be characterised through nonlinear weighting functions, but in the examples described herein, the amount of overlapping between successive or simultaneously appearing stimuli was kept to a minimum, however, persons skilled in the art of multifocal analysis will recognise that overlapping stimuli may have advantages for a particular testing method or application.

Figure 2:
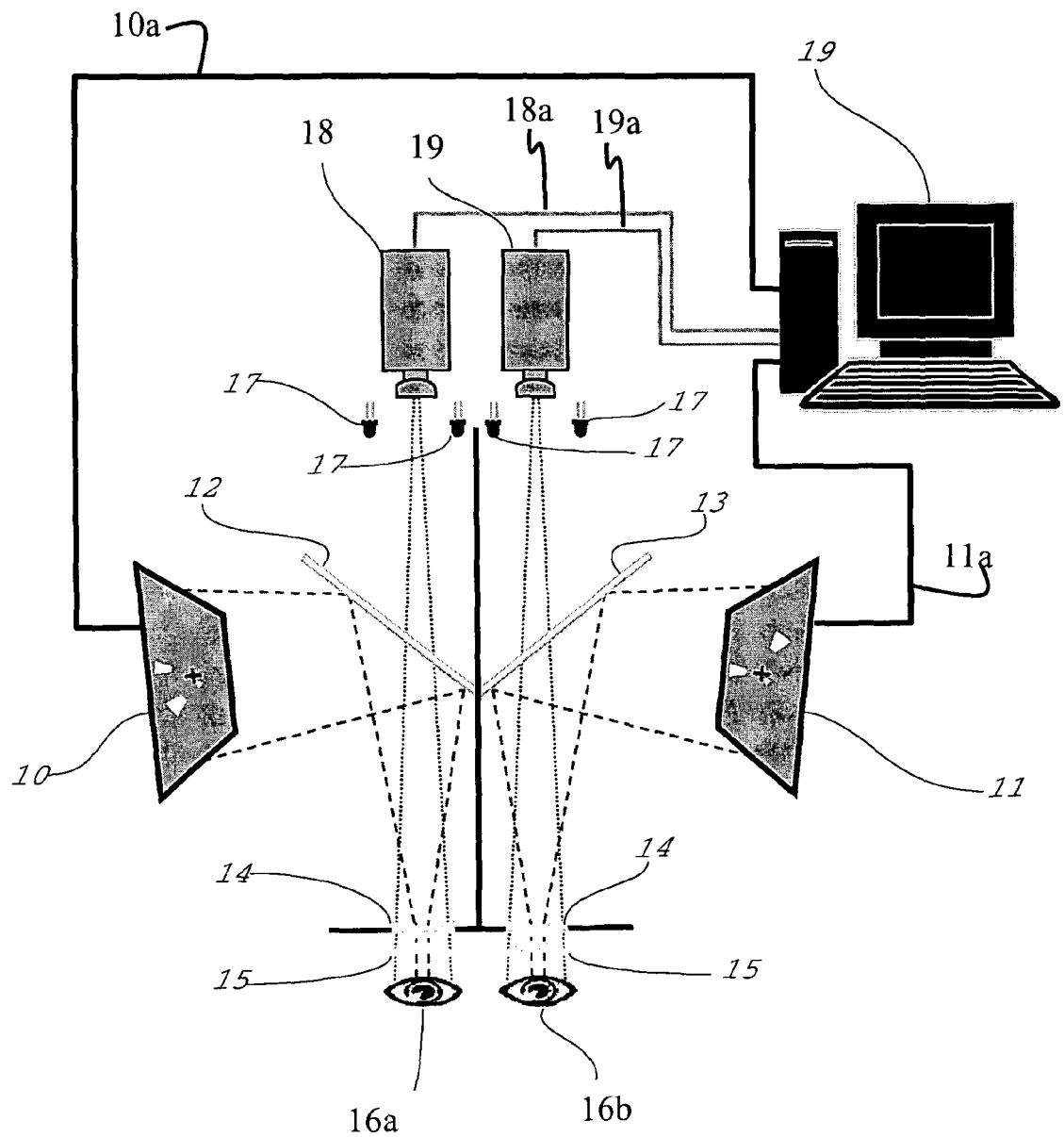
FIG. 2 is an illustration of a particular exemplary arrangement of an apparatus designed to stimulate the two eyes of a subject independently and to independently monitor the responses of each eye's corresponding pupil by video cameras under infrared illumination.

An example of a suitable apparatus for presenting the multifocal stimulus and recording the pupillary responses as per the methods disclosed herein is illustrated in FIG. 2. The stimulus configuration in the present arrangement was a dichoptic one, which provides independent stimuli to the two eyes (that is, each eye sees a different, independently controlled stimulus pattern and or sequence during a test). The independent stimuli for the left and right eyes 16a and 16b respectively were displayed on two liquid crystal displays (LCDs) 10 and 11. Positive lenses 14 of equal focussing power (focal length) are used with the focal length selected such that the displays appear to be at far focus. Corrective lenses 15, possibly of different refractive properties (for example focal length), were provided to correct for refractive errors of the eyes 16a and 16b. Infrared light to illuminate the eyes was provided by light emitting diodes (LEDs) 17, and the pupillary contractions were recorded by detectors 18 and 19 for recording the responses of each eye separately. The detectors may be video cameras, CCD detectors, photodiode detectors, simple power detectors or other suitable detector for recording the reflected infrared light from the subjects' eyes. Two dichroic mirrors 12 and 13 are used to reflect the image of a respective LCD screen to one of the subject's eyes whilst allowing infrared light from the LEDs 17 to pass through to illuminate the subject's eyes and also to allow reflected infrared light to be transmitted through the mirrors to be detected by detectors 18 and 19, and communicated to computer system 19 for analysis by respective communication lines 18a and 19a.

In particular arrangements of the apparatus, a computer system 19 is used to generate stimulus sequences wherein stimuli at particular stimuli regions (for example see FIGS. 1A and 1B) in the particular sequence are transmitted to LCD displays 10 and 11 by respective communication lines 10a and 11a for display to the subjects respective eyes 16a and 16b. In preferred arrangements, the sequence of stimuli displayed on each of the LCD displays is generated independently of each other such that each eye of the subject/patient is tested independently of the other eye (i.e. dichoptic stimulation). Alternatively one may wish to implement a binocular test in which case stimulus regions presented at the same positions in the visual fields of the two eyes would be presented simultaneously. The computer system may also be adapted to record and fit a circle to the lower ¾ (i.e. about 75% or in the range of about 65% to 85%) of pupils with diameters larger than about 3 to 4 mm, thereby providing a measure of the pupil diameters of each of the patient's eyes independently in real time and optionally also to estimate the responses of the retina of each eye to each of the independently modulated stimulus regions that are presented to the two eyes 16 during a particular test. The lower % of the pupil is fitted to a circle because some persons, especially older persons display ptosis, or droopy upper eye lids which can obscure the pupil. For very small pupil sizes fitting the whole pupil may be advantageous given that the upper eye lids would be unlikely to obscure a smaller pupil. The stimuli sequence may be in the form of a video signal which is displayed on the respective LCDs 10 and 11, which may be advantageously presented at 60 frames per second. In the present examples, the detectors 18 and 19 sampled the responses of the pupils of each of the subjects' eyes independently at a rate of 30 frames per second. In the present examples, the sampling of the pupillary responses of the patient by the detectors 18 and 19 was synchronised with every second frame of the stimulus sequence frames displayed on the LCD displays. As described above, each of the subject's pupils receives pooled input from the retina of both eyes in the form of both direct and consensual responses. Hence the pupil contraction recorded by the detectors 18 and 19 provides information about both the direct and consensual responses for each retina.

Pupillary Response Spatial Variation

Figure 3:
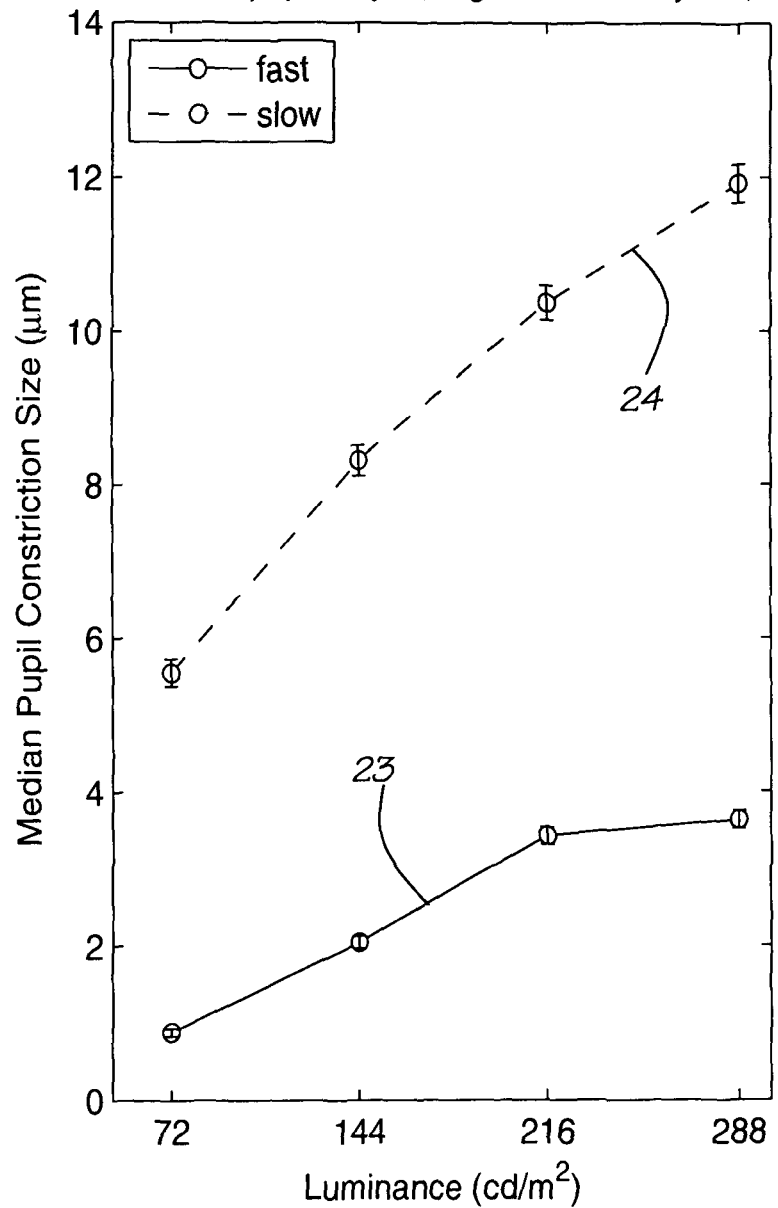
FIG. 3 shows a graph depicting the saturation of the median pupillary contraction size computed across, eyes, pupils, subjects and the 44 regions of the stimulus array of FIG. 1, obtained from 16 normal subjects in responses to 8 stimulus protocols examining pupil size as a function of the maximum luminance of the individual stimuli.
Figure 20:
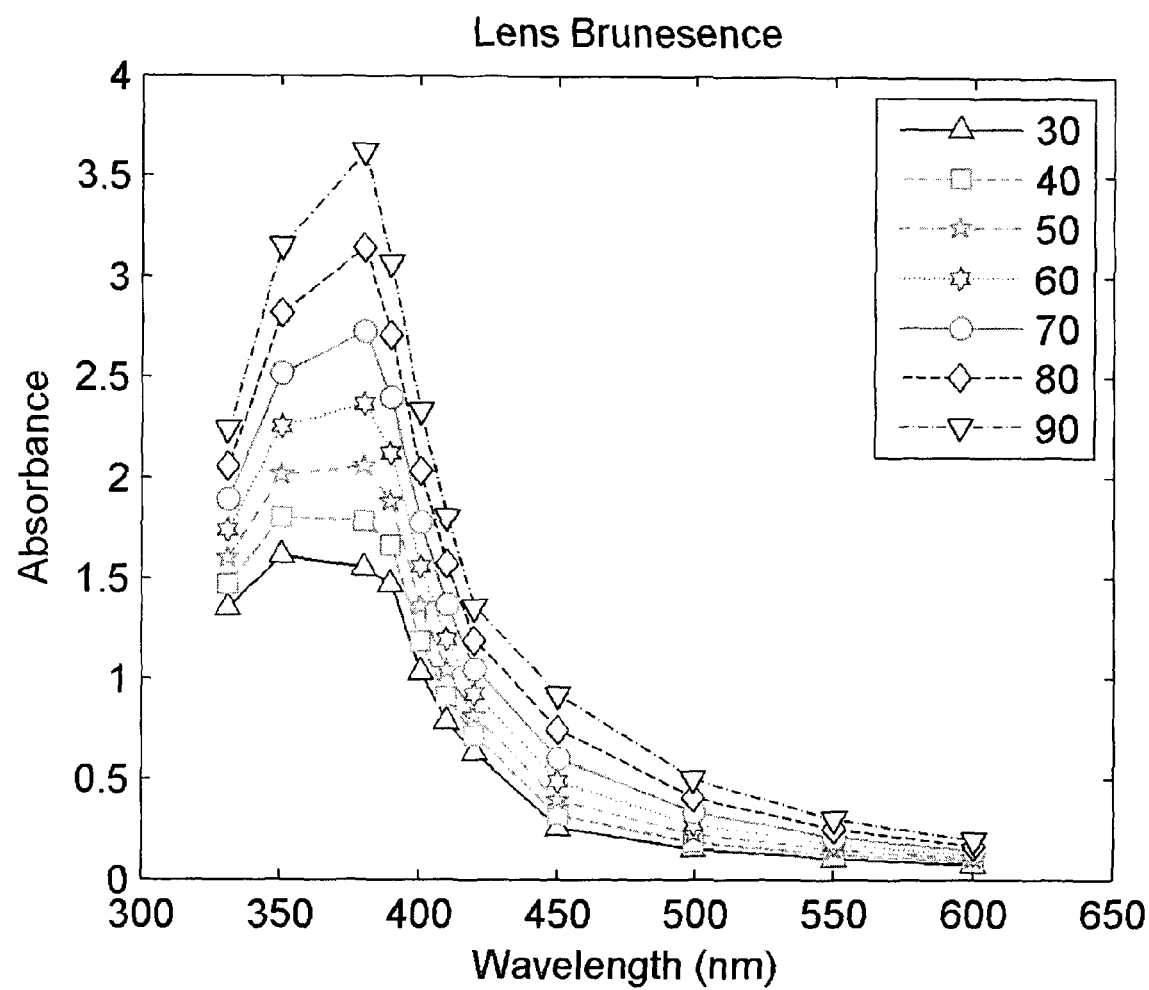
FIG. 20 is a graph of the age-related lens absorbance due to brunescence, one curve for each age in years from 30 to 90.

FIG. 3 shows results from a multifocal presentation of the stimulus array of FIGS. 1A and 1B whose stimulus parameters were varied to define eight variant stimulus protocols wherein tests of 4 luminances are done at each of 2 presentation rates as discussed below. Unlike in FIG. 1 all eight classes of stimuli were yellow, which was used to minimise the effects of the differential absorption in different persons/subjects of blue light which may occur due to differential rates of yellowing (also known as brunescence) of the lens of the eyes of subjects and also as a result of differential absorption of blue light by macular pigments of the subject's retina. Note that white stimulus contains a significant component of blue light whilst yellow stimuli contains little or no blue light component. The yellow stimuli are formed as a combination of red and green stimuli (which contain no blue component, for example from the blue pixels of the LCD displays) and generally have a wavelength of about 590 nm or more generally in the range of about 570 to 600 nm, however, it is accepted that the increased optical absorption of brunescent lenses is primarily at wavelengths below 550 nm [see for example Tomoda A, Yoneyama Y, Yamaguchi T, Kakinuma K, Kawasaki K, Yonemura D., "Spectroscopic studies of brunescent cataractous lenses", FEBS Lett. 1987 Jul. 27; 219(2): 472-6.] therefore using visual stimuli with a wavelength greater than about 500 or greater than about 550 nm (see FIG. 20 for a graph of the age-related lens absorbance due to brunescence) up to about 700 nm would be beneficial in avoiding the effects of brunescent degradation of the lens.

The eight stimulus variants, or protocols, were each tested on 16 visually normal persons i.e. each person was tested eight times, once with each of the different protocols—two presentation rates (fast and slow), each at four different luminance levels. Both of the subject's pupils yield both a direct and a consensual response (since each pupil reports on responses from both retinas) to each of the regions providing 2816 responses for each of the 8 stimulus protocols. The stimulus protocols differed in two ways. The first four protocols contained stimuli that had a mean interval between stimuli present to each region of 1 second; this is referred to as the fast stimulus type. The other four protocols had mean intervals between stimuli at each region of 4 seconds; this is referred to as the slow stimulus type. In all the protocols the stimuli were not presented at periodic intervals, i.e. with a fixed repeated inter-stimulus symbol interval, but rather were presented aperiodically, i.e. at aperiodic intervals, with a selected mean inter-stimulus interval period corresponding to the mean interval of either the slow or fast stimulus type. Also, in all the protocols, when a given stimulus region was presented, it was visible to the subject on the screen for about 33 ms. The contrast of the stimuli may also be temporally modulated during their presentation at rates around 15 to 30 Hz and more generally longer presentation times up to about 0.24 seconds may be employed. Thus, all protocols conformed to the temporally sparse stimulation method described in U.S. Pat. No. 7,006,863, to Maddess & James which also describes in greater detail the effects of presentation rates upon signal to noise ratios for stimuli in the range covered by the fast and slow stimulus regimes. Each of these two groups of protocols was present at one of 4 maximum luminance levels: 72, 144, 216 or 288 cd/m$^2$. The total stimulus duration was 240 seconds, but this was broken up into 8 segments of 30 seconds each.

FIG. 3 shows median pupillary contractions, where the medians are computed across pupils, eyes, regions and over each of the 16 subjects in the present study. These median constriction sizes for each stimulus luminance describe a stimulus/response curve. In fact, as in all examples disclosed herein, the contraction sizes were contractions scaled relative to a constant. The constant was set in the present example to be 3.5 divided by the midpoint of a trend line through the 240 seconds of data for each test. This meant that the pupil contraction sizes were the peak contraction in response to a stimulus scaled as if all pupils had a mean size of about 3.5 mm which was used in the present study to render the scaled pupil sizes to be approximately equal to that of a standard subject, although it will be appreciated that any other scaling factor may be used in accordance with requirements. It is, of course, not necessary to scale the contraction sizes and it will be appreciated that unsealed results may also be used as desired. The main advantages of scaling are that it largely compensates for differences in mean pupil size, especially in older persons who tend to have smaller pupil diameters, and also compensates for pupils that are not circular, since only relative diameter is used.

The error bars on the data points of FIG. 3 are each 99% confidence limits based upon median absolute deviations, the equivalent of standard deviations for medians. The solid curve 23 depicts the stimulus-response curve for the fast stimulus.

Figure 4:
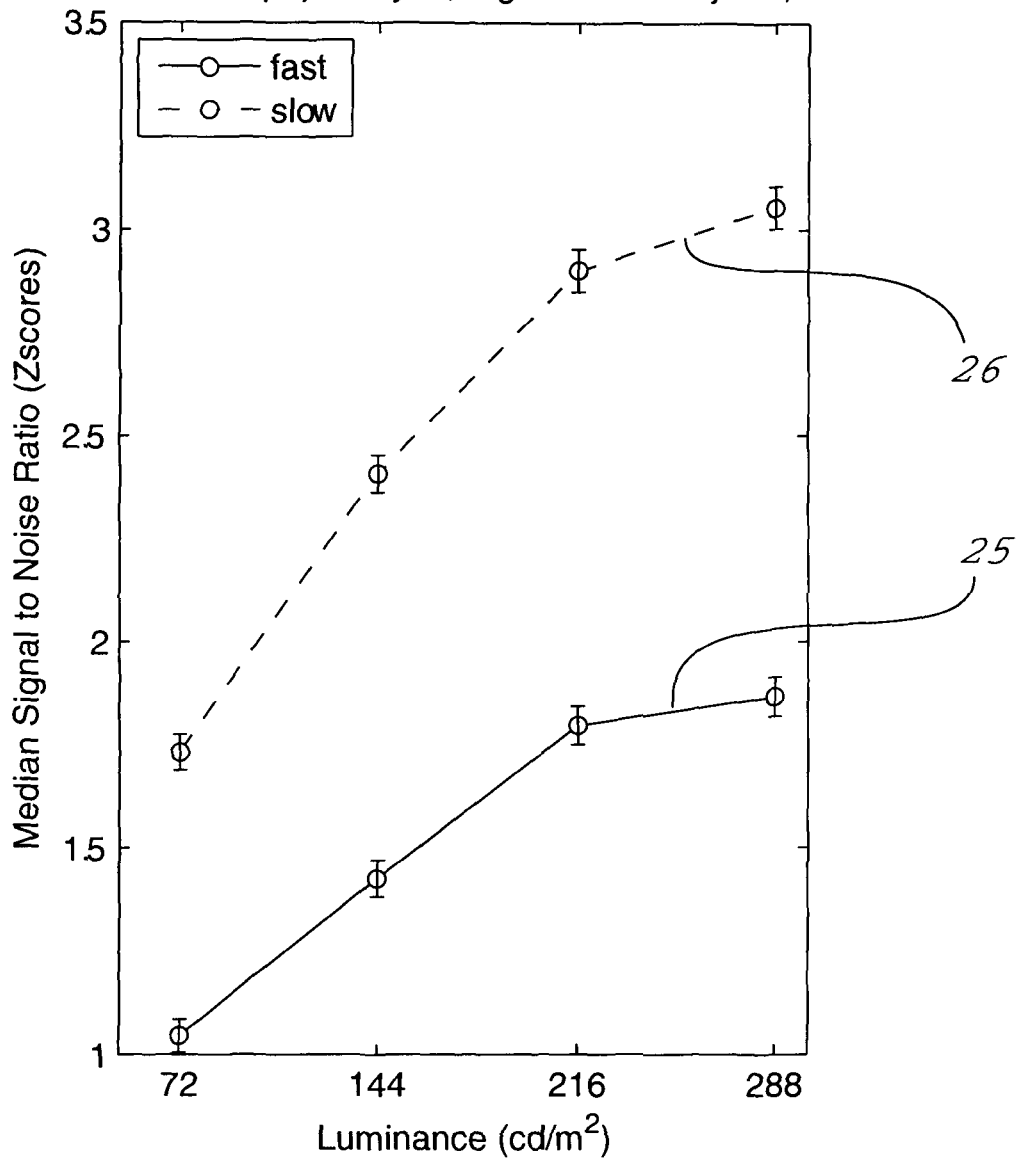
FIG. 4 shows a graph of the same data as FIG. 3 but where the responses are expressed as Z-scores indicating the median signal to noise ratios achieved.

It has been surprisingly found that, at luminance levels of 216 cd/m$^2$ and above, there is clear saturation of the pupillary responses. Larger responses are indicted here by larger pupil contractions recorded in micrometers of peak pupillary contraction. That is, the magnitude of the responses begins to stop increasing in size even though the stimulus grows to 288 cd/m$^2$. As would be appreciated, if a test of the responsiveness of a given part of the retina was desired, then to use a stimulus that was so bright that it totally saturated the pupil response would not be advisable. If a saturating stimulus was used, then regions of somewhat smaller or larger responsiveness would yield the much the same, near maximal saturated response, making it difficult to measure small variations in responsiveness since the ability to detect change at any particular luminance is related to the slope of the stimulus/response curve of the type shown in FIGS. 3 and 4. The responses to the slower stimuli, shown by the points on the dashed line 24 of FIG. 3, show both larger responses and less saturation. FIG. 4 shows the same median response data as that shown in FIG. 3, but where the responses are expressed signal to noise ratios (SNRs) recorded as Z-scores of a normal distribution. The Z-scores thus indicate the number of standard deviations away from zero response and hence indicate the median signal quality and statistical significance. The Z-scores of FIG. 4 also show saturation for both the fast and slow stimulus conditions as seen in plots 25 and 26 respectively. It can be appreciated from the results of FIGS. 3 and 4, when testing the pupillary response using the fast stimuli condition, presenting stimuli which have a maximum luminance of approximately 216 cd/m$^2$ where the SNR is maximal, but where the saturation effects are not significant would be desirable (at least under the present conditions of this example). When testing pupillary responses under the slow stimuli condition, presenting stimuli with maximum luminances of even 150 cd/m$^2$ would still provide SNRs of about 2.4, which on a singled sided test of the significance of the median signal from zero responses would have a p-value of 0.009, which will be appreciated is a high median level of significance.

Figure 5:
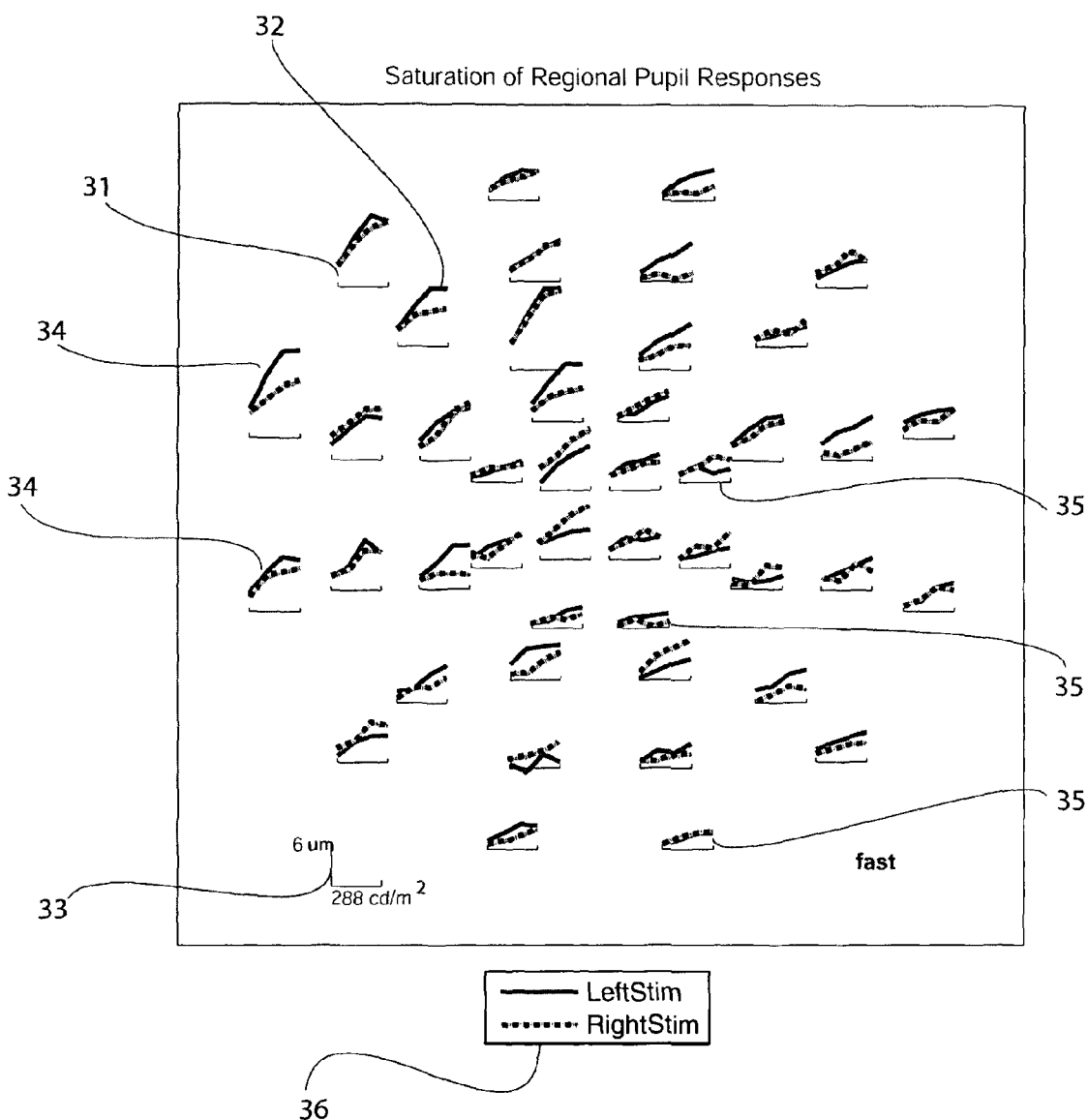
FIG. 5 shows a graph similar to that of FIG. 3 but where the median response sizes to the 4 luminance levels are shown for each region and left and right eye stimuli for the fast stimulus condition presenting stimuli at a mean inter-stimulus interval of 1 s/region.

At first it may seem odd that the responses to the slower stimuli could be large but also show less saturation than the smaller responses to the fast stimuli. This indicates that saturation may occur at two levels, both at the final pupil diameter regulating stage and at an earlier stage, which might differ from region to region. Evidence for this is provided by plots in FIG. 5 where the median response for each luminance and region are computed across subjects and pupils in the fast stimulus condition wherein all the stimuli presented during the tests had mean presentation intervals of about 1 s/region. FIG. 5 shows there is one plot axis for each stimulus region of FIG. 1, each axis being analogous to FIG. 3 but where the data graph only pertains to that stimulus region. Notice that for each plot axis there is one curve plotted for responses to the left eye stimulus (LeftStim) and the right eye stimulus (RightStim) as indicated in the legend 36. The confidence limits are of the same small magnitude as in FIG. 3 but are not shown for clarity of presentation. Note that there is a rough correspondence between the position of the centre of the stimulus regions of FIG. 1 and each of the small plots of FIG. 5. For example plot 31 shows responses from region 37 of FIG. 1A, and plot 32 shows responses from region 25 of FIG. 1B. The axis scale bars 33 indicate the size of a 6 µm pupil constriction on the ordinates of each of the 44 small plots, and that the maximum luminance on the abscissa of each of the small plots is 288 cd/m$^2$, beginning at 72 cd/m$^2$ just as in FIG. 2 and FIG. 3. It has been surprisingly found that some regions (for example region 34 of FIG. 5) can give large, quite unsaturated responses while others (for example region 35 of FIG. 5) can be saturated even at small response levels.

Recall from above that the responses at any particular luminance level are measured concurrently for all stimulus regions. These responses to individual regions therefore reflect responses from the visual fields before they are pooled to produce the overall pupillary response. Hence, as suggested above, saturation occurs separately both before and after pooling. Similar effects are also observed for responses to the four slower stimulus protocols as shown in FIG. 6 where the statically independent multifocal stimuli were presented at a mean interval of about 4 s/region.

Figure 7:
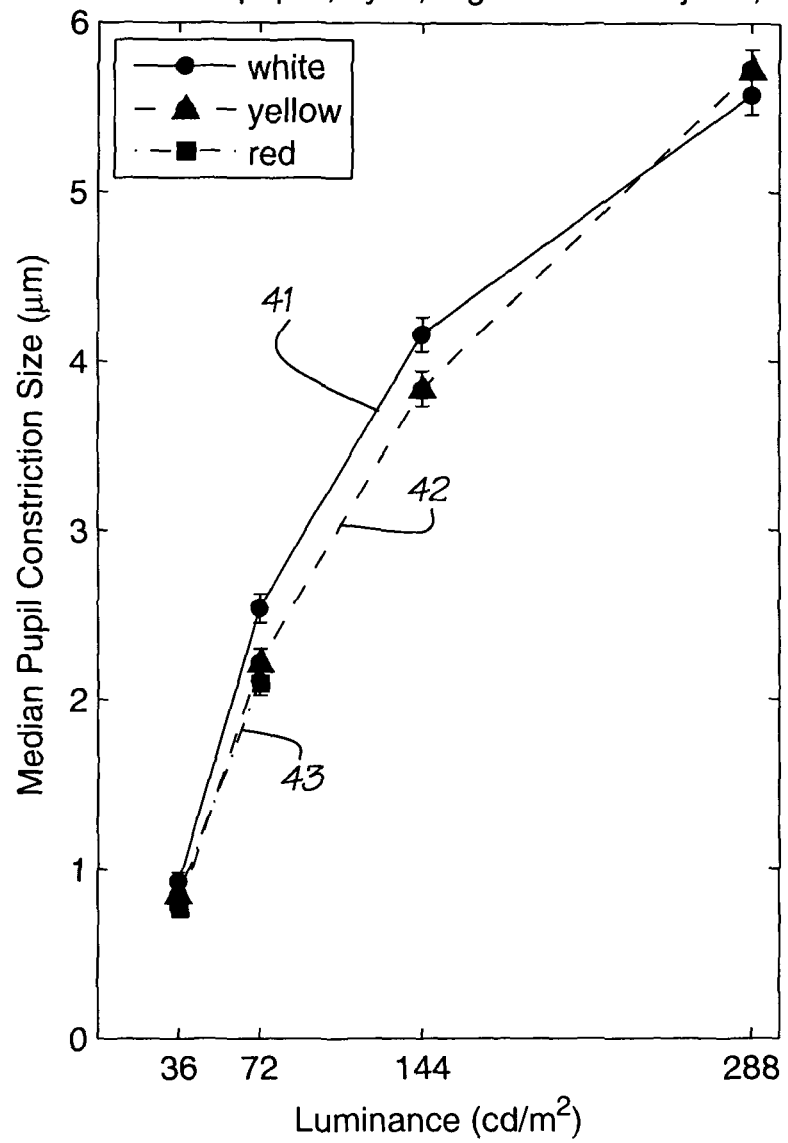
FIG. 7 shows a graph similar to that of FIG. 3 but the data was obtained from a different set of 18 subjects and stimuli of different hue (colour) were presented.
Figure 8:
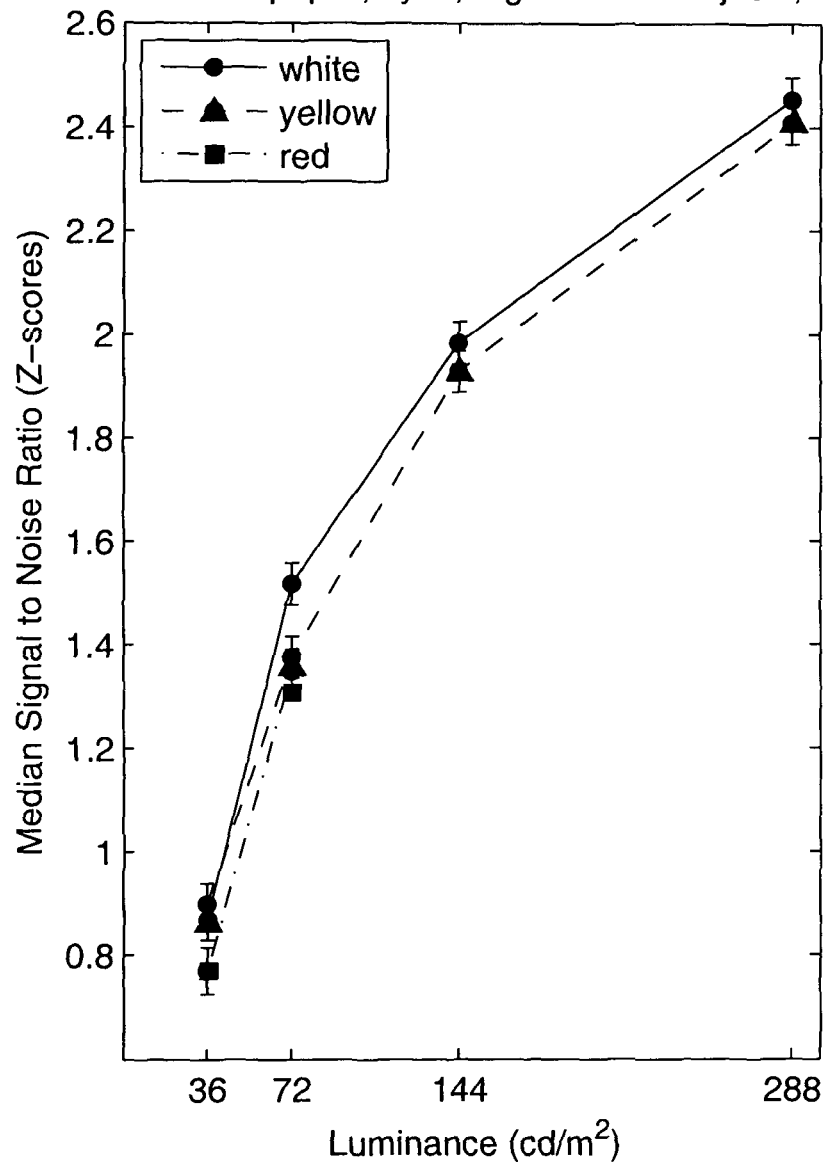
FIG. 8 shows the same data as FIG. 7 but where the responses are expressed as Z-scores indicating the median signal to noise ratios achieved.

A similar set of experiments involving 12 stimulus protocols that were tested on a different set of 18 subjects were also completed. Here the stimuli were only of the fast, mean interval of 1 second type but the stimuli could have one of three different hues or colours: white, yellow and red. For the white and yellow stimuli the luminance levels were 36, 72, 144 and 288 cd/m$^2$. Since the human luminance system is less sensitive to longer red wavelengths the LCD display screens used in this example could only generate red stimuli that had luminances of 36 and 72 cd/m$^2$. FIG. 7 shows the results of the test where the pupil responses are displayed separately for the white, yellow or red (lines 41, 42 and 43 respectively of FIG. 7) stimuli. It can be seen that for all colours, the median response size and saturation of the observed responses depends mainly on the stimulus luminance level rather than the colour. This result would be consistent if, as expected, the main factor in the observed response was due to the parasol cells via the visual cortex given that their gain control system would enhance responses to low spatial frequency dominated, temporally transient, stimuli as used here. It is also expected that the Yellow-ON component of the mcRGCs contributes strongly to the observed pupillary responses. The error bars on the data points in FIG. 7 are each representative of 99% confidence limits. The same conclusions are reached when the data are plotted as Z-scores indicating the median SNRs, as seen in FIG. 8.

Figure 6:
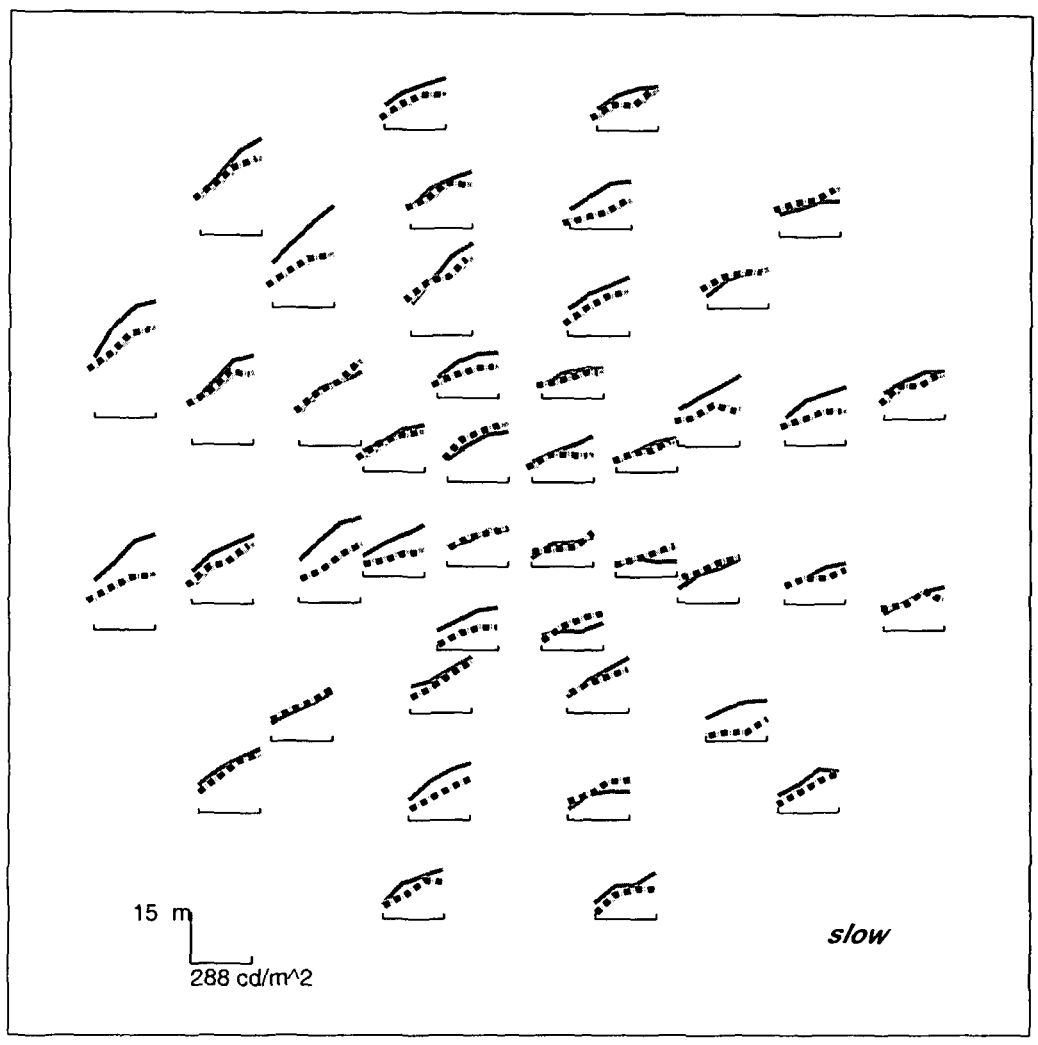
FIG. 6 shows a graph similar to that of FIG. 5 but where the stimuli were presented in the slow stimulus condition presenting stimuli at a mean inter-stimulus interval of 4 s/region.
Figure 9:
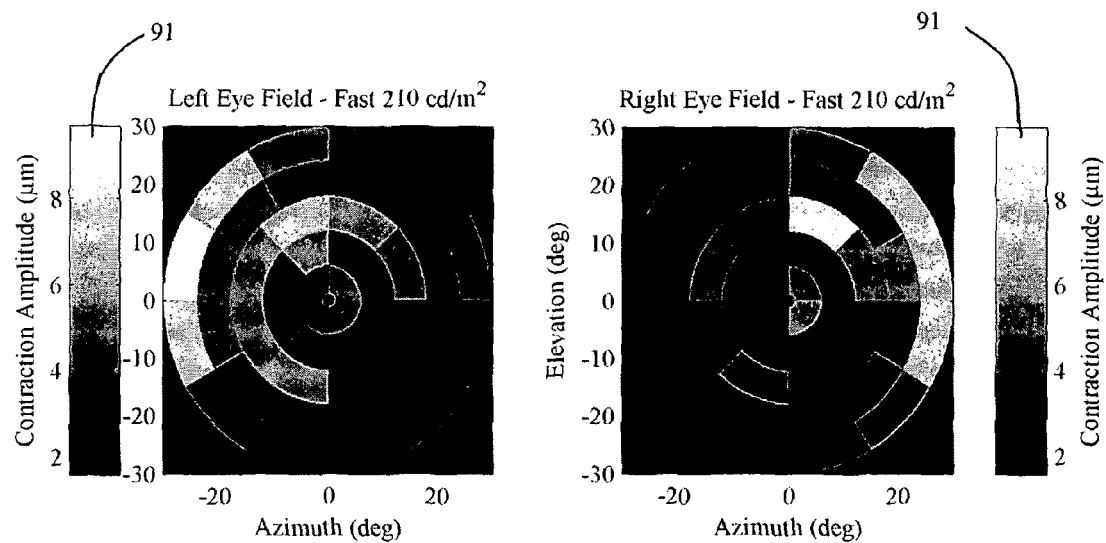
FIG. 9 gives a map of the median responses of 21 normal subjects to a stimulus array like FIG. 1 for a fast stimulus protocol with a mean presentation interval of 1 s/region, where the mapping of the stimulus regions of FIG. 1 to the current presentation format is shown as in FIG. 11, indicating typical variation of the pupillary responses across the visual field.
Figure 10:
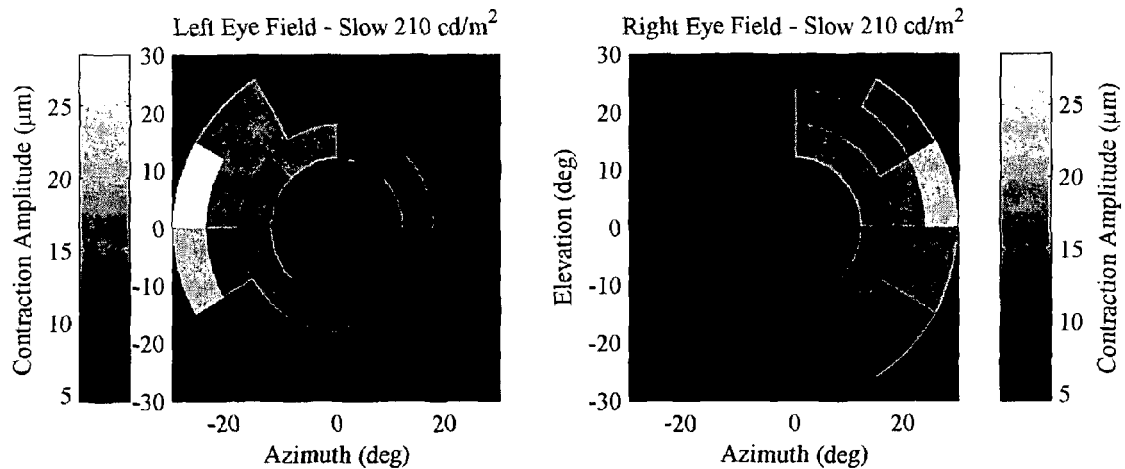
FIG. 10 is similar to FIG. 9 except that the data were obtained with a slow stimulus protocol having a mean presentation interval of about 4 s/region.
Figure 11:
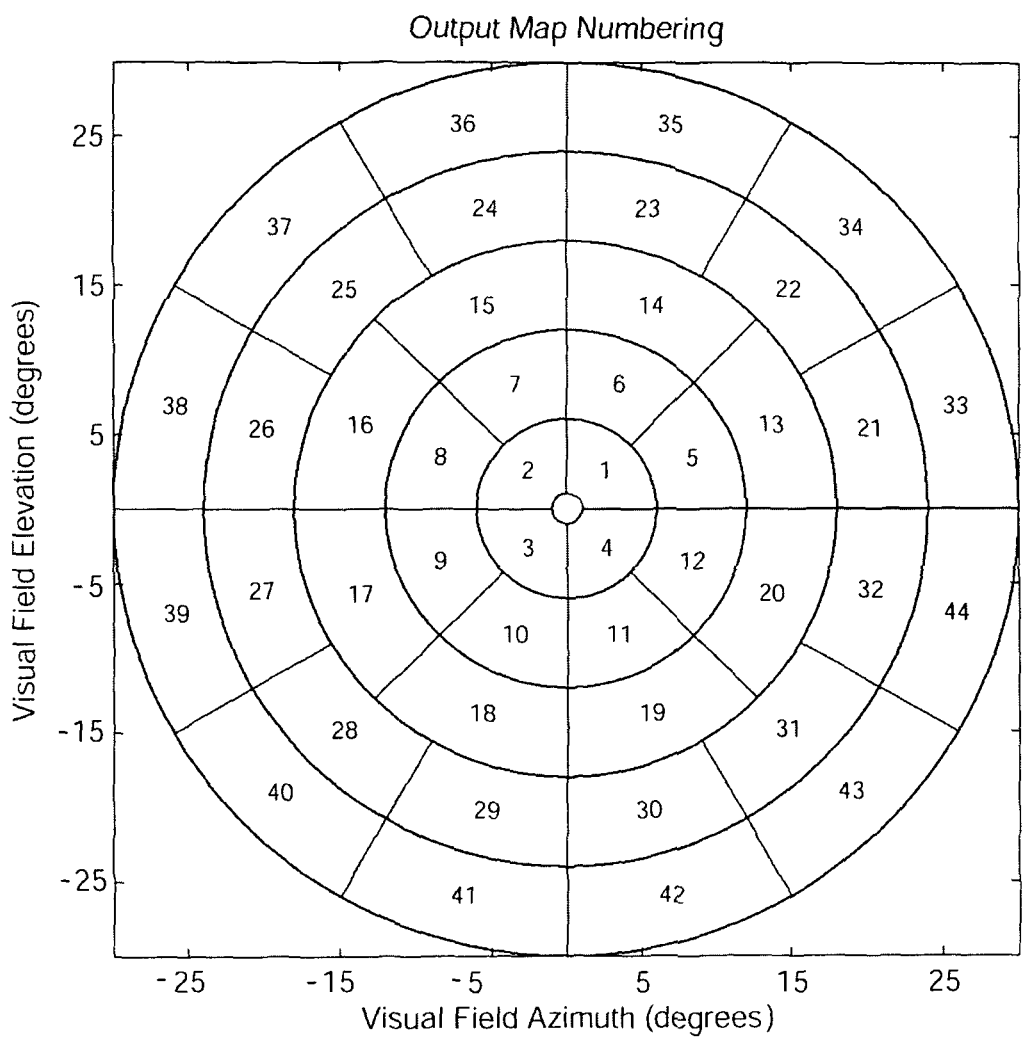
FIG. 11 is a correspondence map between the stimulus region numbers of FIG. 1 and the maps of pupillary responses shown FIG. 9, FIG. 10, FIG. 15A and FIG. 17A.

As can be seen in FIG. 5 and FIG. 6, the size of the pupillary responses produced to any particular luminance level show consistent variations across the field. Additionally the pupil contraction amplitudes show a left-right mirror symmetry between the two eyes and to create FIG. 5 and FIG. 6, right eye data was mirrored about the vertical axis. Hence, the data in FIG. 5 and FIG. 6 had the data from right eyes presented to assume the symmetry of responses shown by left eyes. The data from the two eyes can therefore be said to have been presented in a left eye equivalent mapping. The mirror symmetry is best seen by presenting data separately for the two eyes. FIG. 9 shows the median pupillary contractions from a third set of 21 normal subjects where contraction size is indicated by gray levels. The correspondence between the gray level and contraction response size is shown by the vertical calibration bars 91. Here, the stimuli again had the faster 1 second mean interval but the maximum brightness of each stimulus was 210 cd/m$^2$. It can be seen that the left eye data (left figure) are at least approximately mirror symmetric with the right eye data (right figure), leading to the surprising conclusion that the temporal visual fields, that is the halves of the field closer to the subjects' temples, always give larger responses than the nasal visual fields, that is the halves of the fields closer to the subjects' noses. This is also true for the slower 4 second mean interval version of the stimuli as can be seen in the graph of FIG. 10. Identification of the differences in the responses of the temporal and nasal halves of the visual fields highlights a potential source of error for pupillary visual field testing since the much smaller responses of the nasal visual field leads to the result that the SNRs for these regions are also smaller which gives reduced detection sensitivity in these regions. This significant finding leads to the highly desirable need for methods, and apparatus specifically adapted for implementation of such methods, to increase the responses of these and other less responsive regions of the visual field to pupillary response testing methods. Note that, in FIG. 9 and FIG. 10 the layout of the regions does not correspond exactly to that of FIG. 1. Instead, the non-overlapping regions shown here are roughly centred on the positions of the actual (sometimes overlapping) stimulus regions of FIG. 1. The exact correspondence between the regions is shown by the numbering scheme outlined in FIG. 11, which shows which region numbers in FIG. 1 corresponding to the region numbers in FIG. 9 and FIG. 10.

Pupillary Response Gain Control Mechanism

Figure 12:
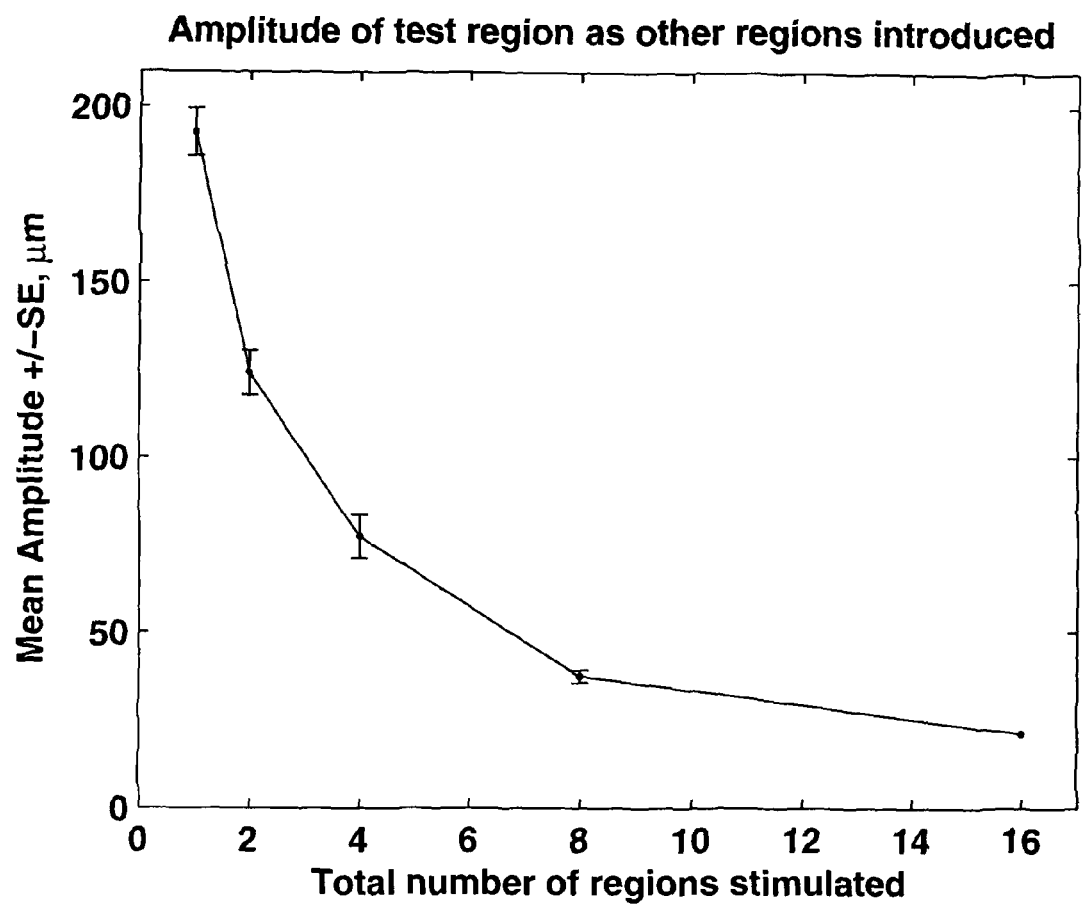
FIG. 12 shows that as the number of stimuli presented to the visual field increases, the gain of the response to a probe stimulus decreases, indicating the presence of a gain control mechanism that acts to keep the mean pupil size relatively constant for a given person, light and accommodative level.

A further surprising effect has been the discovery by the inventors of a gain control mechanism operating at the level of the pooling of the individual response regions in the creation of the signal driving the pupil. This is illustrated in FIG. 12 which shows the pupil contraction size obtained to identical stimulation of a single probing test stimulus region as a function of the total number of active stimulus regions (1, 2, 4, 8 and 16 regions are shown), that is as more stimulus regions are included in the test. Background luminance was 10 cd/m$^2$, the maximum luminance of each of the stimuli was 290 cd/m$^2$, and all stimuli were presented at a mean interval of 0.5 seconds in each test region. The regions tested were a selection from those shown in FIG. 1. It is clear that as the number of stimulated regions increases the response to each individual stimulus decreases. This indicates a gain control mechanism which reduces the response gain per region when more stimuli are present. The consequences of this gain control mechanism are described in greater detail below.

For a given person, and at a given ambient light level, their pupil has a capacity to respond to stimuli (eg, visual, auditory or other) which is proportional to the mean pupil size K. In the present system there are N stimuli, $s_i$, presented to an eye. For a given number of test regions being shown there is a particular gain, g. The responses within the brain, $r_i$, to these stimuli are a function or functions of the $s_i$, that is, $r_i = f(s_i)$. By inspection of FIG. 5 and FIG. 6 it can be seen that the stimulus/response functions are approximated by a power law, that is $f(s_i) \approx a \, s_i^z$, where the exponent z is less than 1 (it is noted that the exponent most likely differs in each of the individual regions of the visual field, however, for simplicity in the present examples, the same exponent has been used in all regions). The results presented in FIG. 12 indicate that the $f(s_i)$ are pooled together prior to application of a multiplicative gain factor, g, before the result is sent via the fibres of the oculomotor nerve (cranial nerve III), each of the subject's eyes to control the fluctuations in the pupil diameter caused by a given stimulus $s_i$. Given that, for particular lighting, subject and accommodative conditions, the mean pupil size is approximately constant, K, then approximating the pooling process as a simple summation the mean pupil responses as be described as:

$$K = g\Sigma_{i=1}^{i=N} f(s_i)$$

indicating that the size of the response to a given $s_i$ depends on all the other responses.

For the kth stimulus, $s_k$, this can be written as:

$$gf(s_k) = K - (g\Sigma_{j=1}^{j=M} f(s_j)_{j \neq k})$$

and the pooled of the responses to the $s_{j \neq k}$ can be written as $P_{j \neq k}$, providing $$gf(s_k) = K - P_{j \neq k}$$

From this formulation, the combination of the gain control and the limited capacity of the pupil to respond at any pupil size leads to the conclusion that, for a given response $f(s_k)$ to be increased in size, the others, $P_{j \neq k}$, must be made smaller. Fortunately, as shown in FIG. 5, FIG. 6, FIG. 9 and FIG. 10 many of the responses, particularly those responses from the temporal visual fields are very large. Therefore if the stimuli $s_k$ for those regions were made less effective, then the responses of all the other regions may be increased.

Correlation of the results of FIG. 12 with the proposed model equations above, it can be deduced that reducing the luminance of the strongly responding regions, such as those of the temporal visual fields, consequently reduces the overall pooled response. This in turn reduces the effects of the gain control mechanism which acts to reduce pupil gain when presented with large sensory drive supplied to the pupils. This would increase the proportion of the total pupil response contributed by the more weakly responding regions.

Balanced Stimuli

To demonstrate the effect of the pupillary response gain, a study with 4 stimulus protocols was designed. Two of these protocols were designed such that they exhibited a regional luminance balancing scheme whereby the luminances of each region were weighted so as to reduce the brightness, and so to the contribution to the pooled response of the more responsive regions. One of the balanced stimulus protocols operated at the fast stimulus mean rate of about 1 second per region) and the other at the slow stimulus mean rate of about 4 second per region (see U.S. Pat. No. 7,006,863, to Maddess & James). The remaining two protocols were designed to minimise the saturating proportion of the stimulus/response curves, as illustrated by FIG. 3 to FIG. 8 by using a stimulus ensemble like that of FIG. 1 which had a maximal luminance for each of the 44 regions of about 210 cd/m$^2$, again one each operating in the fast and slow stimulus regimes. From FIG. 4 it can be seen that mean luminances in the range of about 100 to about 240 cd/m$^2$ would be reasonable stimuli for presentation rates about equal to those used here.

To determine the required region-wise luminance balancing attenuations a further set of 35 normal subjects was tested with a fast, mean interval 1 second, stimulus protocol where the maximum luminance was 290 cd/m$^2$. The median pupil contraction responses of these subjects were computed for each region. On the assumption that the individual regions respond linearly to luminance, the correct set of weight would be achieved by transforming those median across subjects responses to decibels, dB=10 $\log_{10}$(response), and then attenuating the maximum brightness of each region by its corresponding decibel weight. These attenuations are shown with their corresponding left eye region numbers in the "Linear (dB)" column of Table 1 below.

Closer analysis of the region-specific data presented in FIGS. 5 and 6 indicates that the responses saturate according to a relationship similar to a power law relationship between luminance and response of the form:

$$\text{Response} = K \times \text{Luminance}^z,$$

or more generally:

$$\text{Response} = K \times \text{Stimulus}^z,$$

where the coefficient, z, is less than 1 or greater than 1.

A reasonable approximation would therefore be to multiply the decibel attenuations best suited to linear stimulus/response functions by about 0.3 to 0.8. For this demonstration 0.5 was selected. Multiplying the decibel attenuations by 0.5 is equivalent to assuming the exponent z for the power law is 0.5, that is the square root of the linear attenuations. These new square root attenuations are shown in the "Square Root (dB)" column of Table 1 below. This is a non-limiting design and an obvious extension of this method would be to fit a mean exponent all regions and use that to specify the attenuations, or alternatively to fit separate exponents for each region and use them to provide a different coefficient for each region. Alternatively some function other than a power law might be used, to take account of the stimulus/response function shape when defining the attenuations. Note that for some stimuli, for examine non-visual stimuli that effect changes in pupil size the shape of the stimulus/response function might be quite different. The present non-limiting method is merely designed to demonstrate the principle.

With a maximum luminance of 290 cd/m$^2$ in the unattenuated regions, that is regions 11 and 30 that had attenuations of 0 dB, the mean luminance of the individual regions was 210.35 cd/m$^2$, similar to that of the unbalanced stimuli. The median luminance of the balanced region stimulus ensembles was 205.35 cd/m$^2$. To the extent that the mean pupil size depends on the global mean luminance, all four stimulus protocols would be expected to provide the same mean pupil size.

Figure 13:
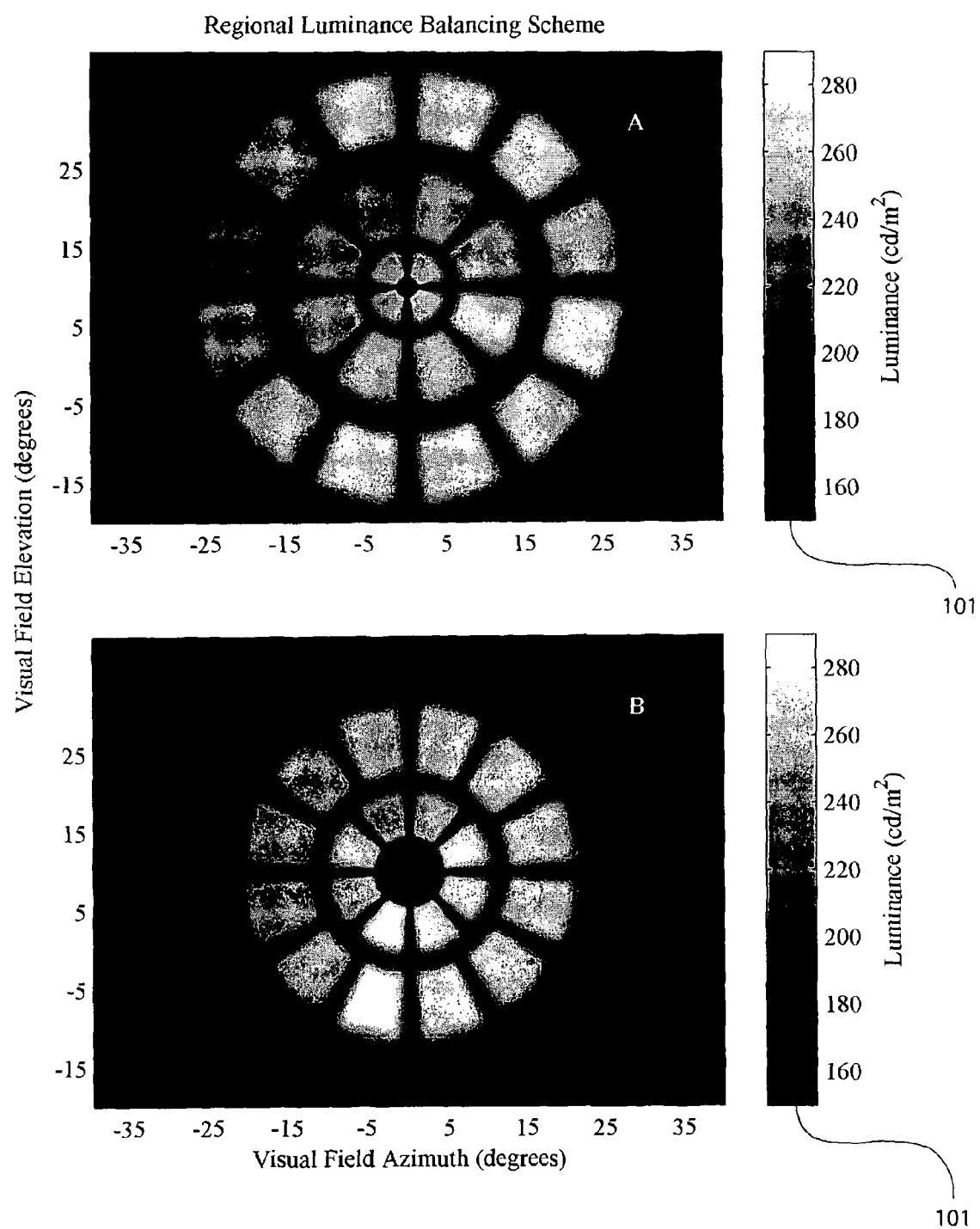
FIG. 13 shows an exemplary arrangement of a balanced stimulus ensemble wherein the mean luminance of each of the individual stimuli is set utilising a square root balancing system.

An example of a version of this square root balanced stimulus ensemble is shown in FIG. 13. The spatial layout is very similar to FIG. 1, being illustrated for here for a left eye stimulus, but now the regions that respond more strongly, particularly those in the temporal field, are dimmer. The maximum luminance of each of the regions of the balanced stimulus can be appreciated by inspecting the vertical calibration bars 101.

TABLE 1

| Region | Linear (dB) | Square Root (dB) |
|---|---|---|
| 1 | 4 | 2 |
| 2 | 4 | 2 |
| 3 | 3 | 1.5 |
| 4 | 4 | 2 |
| 5 | 2 | 1 |
| 6 | 4 | 2 |
| 7 | 3 | 1.5 |
| 8 | 1 | 0.5 |
| 9 | 2 | 1 |
| 10 | 1 | 0.5 |
| 11 | 0 | 0 |
| 12 | 3 | 1.5 |
| 13 | 5 | 2.5 |
| 14 | 6 | 3 |
| 15 | 4 | 2 |
| 16 | 4 | 2 |
| 17 | 2 | 1 |
| 18 | 3 | 1.5 |
| 19 | 3 | 1.5 |
| 20 | 4 | 2 |
| 21 | 4 | 2 |
| 22 | 4 | 2 |
| 23 | 3 | 1.5 |
| 24 | 2 | 1 |
| 25 | 2 | 1 |
| 26 | 2 | 1 |
| 27 | 2 | 1 |
| 28 | 2 | 1 |
| 29 | 1 | 0.5 |
| 30 | 0 | 0 |
| 31 | 3 | 1.5 |
| 32 | 4 | 2 |
| 33 | 7 | 3.5 |
| 34 | 5 | 2.5 |
| 35 | 3 | 1.5 |
| 36 | 2 | 1 |
| 37 | 2 | 1 |
| 38 | 3 | 1.5 |
| 39 | 1 | 0.5 |
| 40 | 2 | 1 |
| 41 | 2 | 1 |
| 42 | 2 | 1 |
| 43 | 3 | 1.5 |
| 44 | 5 | 2.5 |

EXAMPLE

The four stimulus protocols, providing stimuli that were balanced or not balanced with mean presentation intervals of either 1 or 4 seconds, were tested on 21 normal subjects and 21 subjects with primary open angle glaucoma. The two groups of subjects were age and sex matched. The glaucoma patients had at least one eye whose visual field severity was rated as being either moderate or severe. These severity classifications are standard and were based on the so called mean defect (MD) of visual field data obtained from a Humphrey Field Analyser II (HFA II). The HFA II is widely regarded as the standard subjective perimeter. The MD is a weighted mean of the decibel deviations from normative data in sensitivity across the portion of the visual field measured.

In the present example, a 24-2 pattern of the HFA II was used to test all the subjects. The 24-2 pattern tests locations on a 6 degree square lattice of points all inside the central 24 degrees of the visual field. A moderate field was one with a MD≥6 dB and <12 dB and severe fields had MDs of >12 dB.

The purpose of including glaucoma subjects was to determine not only if the balancing method improved the response sizes of less responsive regions, but also to see if this translated into better ability to detect changes in visual fields, whether for assisting with diagnosis, treatment management, or detecting small variations in normal and non-disease associated aspects of visual fields or other functions which can be measured by physiological responses.

It is found that the balancing strategy significantly improves the response size in normal subjects. To demonstrate this, pupil constriction data obtained from normal subjects was submitted to a multivariate linear model. The data were first transformed to decibels by a generalized logarithmic transform with a lambda value of 10. The linear model examined various independent effects that might determine the observed responses. The data from the fast and slow protocols were compared separately. Included in the fit were factors for each left eye equivalent region, and also an interaction between each region and the balancing condition. This balancing interaction condition was fitted as contrast so that the main regional effects were the means across subjects, pupils and eyes for the reference unbalanced condition and the interactions gave the differences from the reference condition. T-statics for each of these interactions therefore indicated the significance of the difference from the reference unbalanced condition at each of the 44 visual field regions/eye that were tested.

Figure 14:
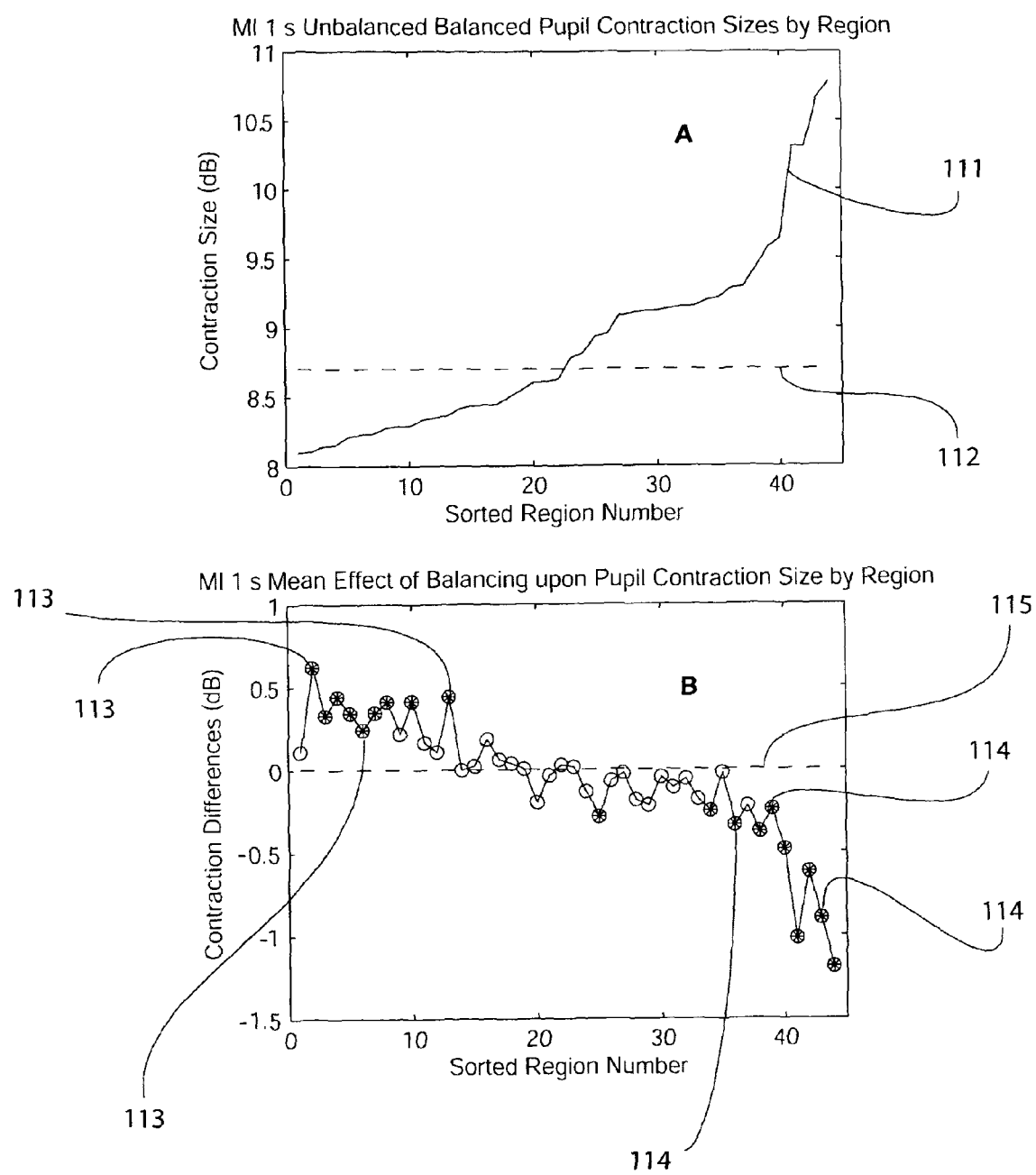
FIG. 14A shows a graph of the mean pupil response sizes in decibels of the 44 regions of an unbalanced stimulus ensemble to a fast stimulus protocol measured in 21 normal subjects sorted by region from least responsive to most responsive.
FIG. 14B shows a graph of the changes due to balancing the multifocal stimuli, expressed as decibel differences from the unbalanced condition, due to stimulation with the balanced stimulus ensemble shown in FIG. 13; again sorted in the same order as the data of FIG. 14A.

FIG. 14A shows a plot 111 of the fitted mean reference responses from the 44 regions per eye sorted from smallest to largest. Note that the presentation order is taken from the sort order of FIG. 14A, it is not the case the data in 14B are themselves sorted. That is, if the data of the upper graph were originally d=[3 5 4], the sort order is s=[1 3 2] so that d(s)=[3 4 5]. A new data set G=[X D F], if sorted in the same order as d gives G(s)=[X D F]. In the present case the sort order of FIG. 14A is applied to the data of FIG. 14B so that they are comparable by inspection. Given that the reference condition was the unbalanced case, these responses show the usual bias towards some regions giving larger responses than others. The dashed horizontal line 112 is the median regional response level of about 8.7 dB.

FIG. 14B shows the fitted interaction contrasts sorted in the same way. The ordinate shows the contraction difference caused by the balancing strategy. The regions with smaller responses in the unbalanced case, on the left side of the plot, show larger responses in the balanced case. The regions 113 with positive contraction differences, indicating larger responses to balanced stimuli are significantly different at p=0.05 or less. Similarly the regions 114 with negative contraction differences, indicating smaller responses to balanced stimuli, are also significantly different at p=0.05 or less. The horizontal dashed line 115 indicates the level of no change from the unbalanced condition.

These results are consistent with the proposed model above of the pupil gain control system. That is, decreasing the luminance of stimuli that are presented to more responsive regions in the visual field reduces the contributions to the overall pooled driving signal to the, thereby increasing the absolute response size of normally less responsive regions.

Figure 15:
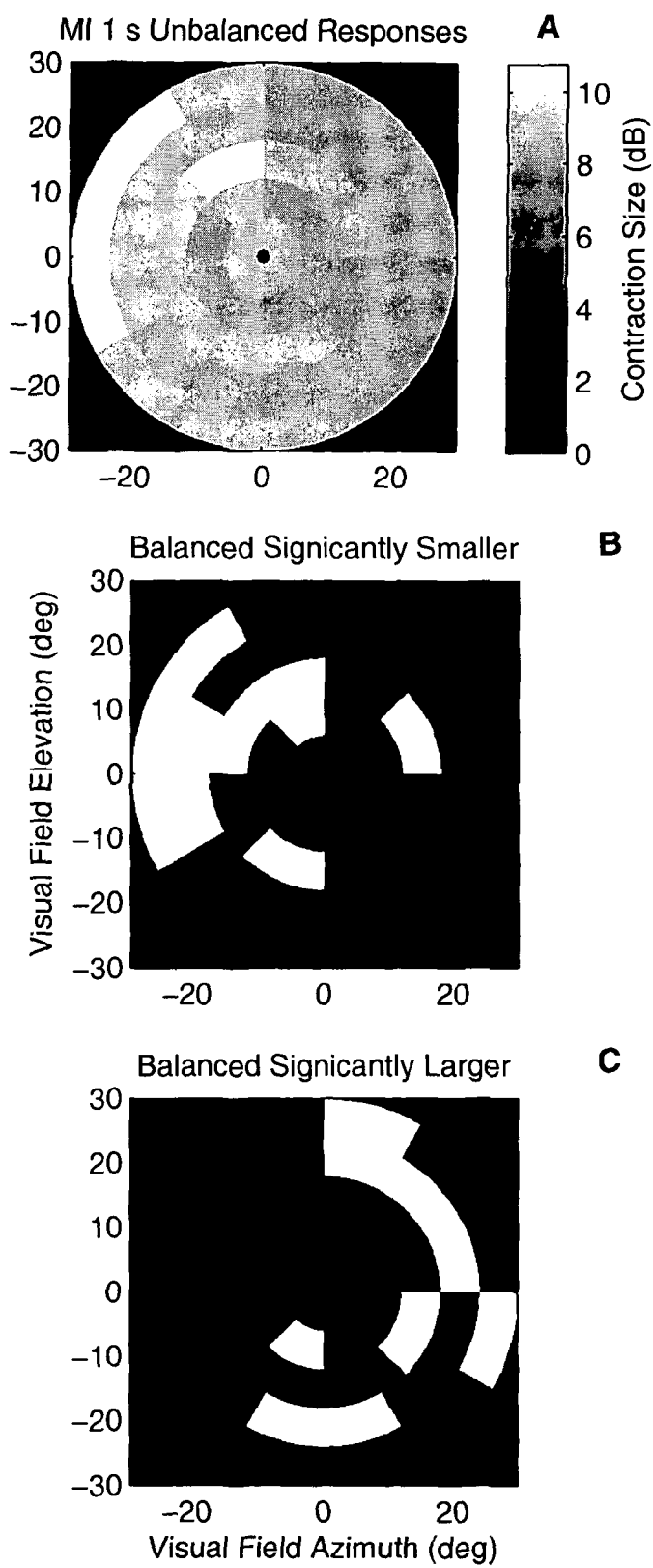
FIGS. 15A to 15C respectively show: the mean unbalanced data by region for the fast stimulus protocols; those regions in the visual fields whose pupillary responses were significantly decreased by balancing; and those regions whose pupillary responses were significantly increased by balancing.

The mean decibel responses of normal subjects to the unbalance fast stimulus are shown in left eye format in FIG. 15A. Like FIG. 9 and FIG. 10 this response map uses the method of FIG. 11. This is the same data as FIG. 14A but presented in a two dimensional visual field map. Again larger responses are found in the temporal rim of the visual field. Using the same mapping as FIG. 15A the regions with responses that were significantly decreased by the balancing method are shown in white in FIG. 15B. Similarly the regions whose responses were increased by the balancing method are shown in white in FIG. 15C.

Figure 16:
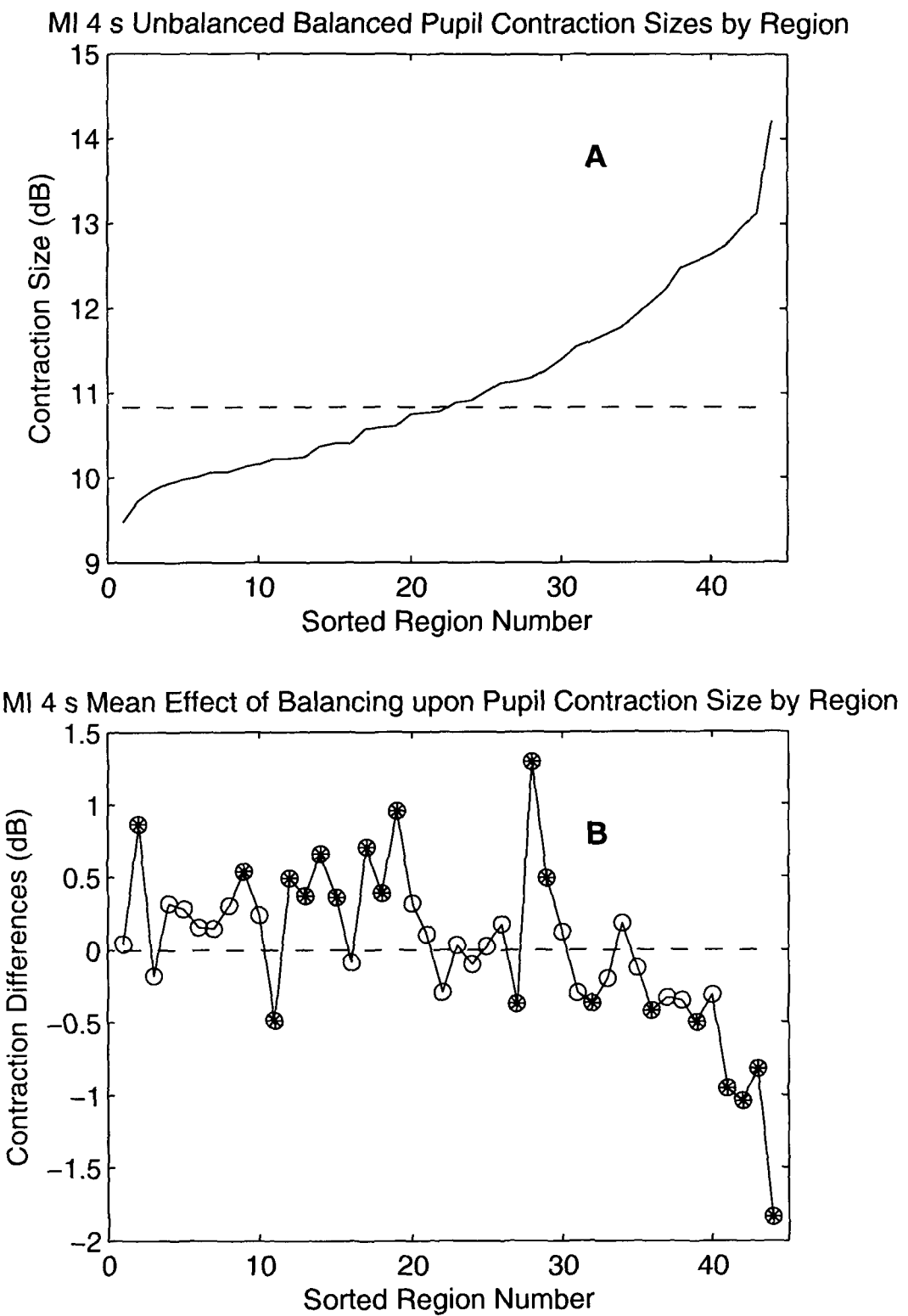
FIG. 16A shows a graph of the mean pupil response sizes in decibels of the 44 regions of an unbalanced stimulus ensemble to a slow stimulus protocol measured in 21 normal subjects, sorted by region from least responsive to most responsive, where the region number is identified in FIG. 11.
FIG. 16B shows a graph of the changes due to balancing the multifocal stimuli, expressed as decibel differences from the unbalanced condition, due to stimulation with the balanced stimulus ensemble shown in FIG. 13; using the sort order of FIG. 16A.
Figure 17:
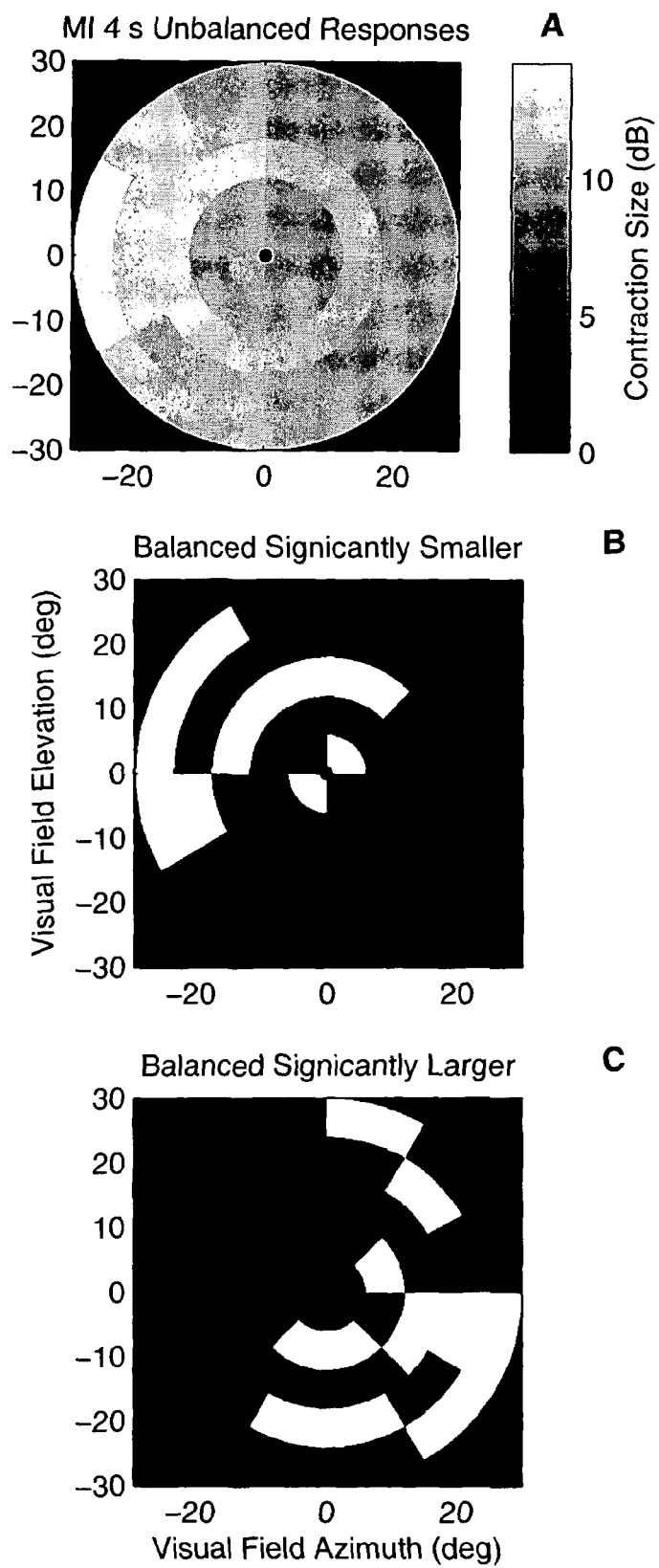
FIGS. 17A to 17C respectively show: the mean unbalanced data by region for the slow stimulus protocols; those regions in the visual fields whose pupillary responses were significantly decreased by balancing; and those regions whose pupillary responses were significantly increased by balancing.

The same square root balancing method was used for the slower stimuli. Since this balancing method was based on data from 35 normal subjects from a fast stimulus protocol it may not have been optimal for the slower stimuli. Nevertheless, the same general pattern was found. FIG. 16A shows the sorted mean responses of the unbalanced condition. FIG. 16B shows the regions that increased or decreased their responses where the regions have been sorted in the same way as in FIG. 16A. Again regions with large responses tend to decline and those with smaller responses tend to increase. This is easily seen in FIG. 17 which follows the same logic as FIG. 15.

TABLE 2

| Fitted Variable | Coeff (dB) | SE (dB) | t-stat | P |
| --- | --- | --- | --- | --- |
| Pupilside | 0.009 | 0.018 | 0.48 | 0.631 |
| Stimside | −0.087 | 0.018 | −4.89 | 0.000 |
| Consensual × Temporal | −0.286 | 0.025 | −11.41 | 0.000 |
| Consensual × Nasal | −0.046 | 0.025 | −1.82 | 0.069 |
| Female | −0.184 | 0.018 | −10.20 | 0.000 |
| DecadeRel60 | 0.141 | 0.013 | 10.69 | 0.000 |

As mentioned above, other independent effects were also simultaneously fitted in the linear models used here. This was done to ensure that the regional visual field effects found were not confounded with other significant sources of variance. Table 2 above summarises the other effects for the linear model characterising the responses to the two fast stimulus protocols (one with balanced stimuli and one without), showing the probability (P) of a significant effect. Values of 0.000 indicate P<0.0005.

As can be seen from Table 2, there is no significant effect of which pupil was recorded (Pupilside), or the nasal half of the visual field recorded by consensual responses (left pupil reporting the right eye, or right pupil reporting on the left eye) recorded in the nasal visual field (Consensual×Nasal). There was a small effect of the stimulus side (Stimside), left stimuli giving responses that were −0.87 dB smaller (0.9802× smaller) although this is probably an artefact of only having 21 normal subjects in the test. Alternatively, this may be related to a genuine effect of the handedness of the subjects, mainly right handed, and or an effect of eye dominance, which tends to follow handedness. In other data sets these effects have been found to be significant. The temporal half of the visual field gave smaller responses for the consensual rather than the direct responses (Consensual×Temporal), this is a well known effect and was highly significant, having a t-statistic of −11.41. Females had slightly smaller responses than males, and there was a small effect of the covariate age that was 0.141 dB per decade of age relative to 60 years, or 1.4 dB per century.

The comparable results for the slow stimuli are shown in Table 3 below. The results were very similar although there was no effect of being female, the Consensual×Temporal effect was larger, and the age effect was smaller.

TABLE 3

| Fitted Variable | Coeff (dB) | SE (dB) | t-stat | P |
| --- | --- | --- | --- | --- |
| Pupilside | 0.015 | 0.027 | 0.55 | 0.582 |
| Stimside | −0.078 | 0.027 | −2.86 | 0.004 |
| Consensual * Temporal | −0.647 | 0.038 | −16.93 | 0.000 |
| Consensual * Nasal | −0.127 | 0.038 | −3.33 | 0.001 |
| Female | −0.010 | 0.028 | −0.36 | 0.721 |
| Fs | 0.185 | 0.027 | 6.85 | 0.000 |
| DecadeRel60 | −0.050 | 0.020 | −2.49 | 0.013 |

A common way of characterising the diagnostic efficacy of a test is to produce a receiver operator characteristic (ROC) plot and then compute the area under the curve (AUC). An area of 1 indicates perfect diagnostic performance in which all patients are correctly diagnosed, perfect diagnostic sensitivity, while no normal subjects are misdiagnosed, that is a false positive rate of 0. An area of 0.5 indicates chance performance. Sometimes, as here, these areas are reported as percentages where 100% corresponds to perfect diagnostic performance (efficiency).

To examine the diagnostic efficacy of the 4 stimulus protocols, normative data was created by fitting mean effects of region, sex and consensual—temporal visual field. Direct and consensual responses for each eye were compared and the response set with the best SNR for of these two was selected subject-wise. Deviations from the normative data were then computed for both normal and glaucoma subjects. For each eye, the 44 deviations per eye were sorted and then ROC plots were computed for the mean of the first N worst regions.

Figure 18:
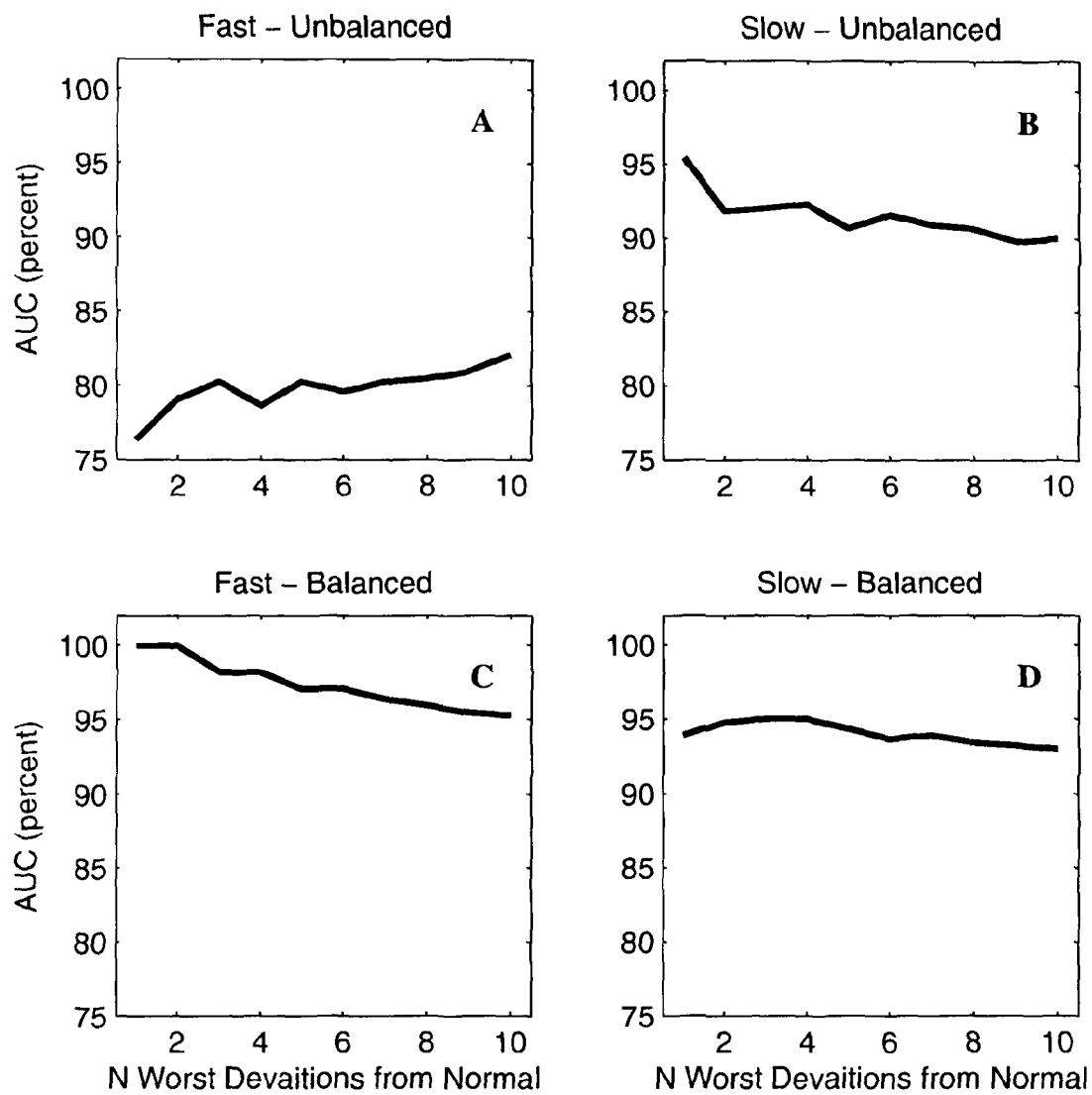
FIG. 18 shows the percent area under curves (AUC) from receiver operator characteristic (ROC) plots for the four stimulus protocols in which normal and glaucoma subjects were tested, wherein for each eye, the deviations from normative data were sorted and then ROC plots were constructed for the N-worst deviations.
Figure 19:
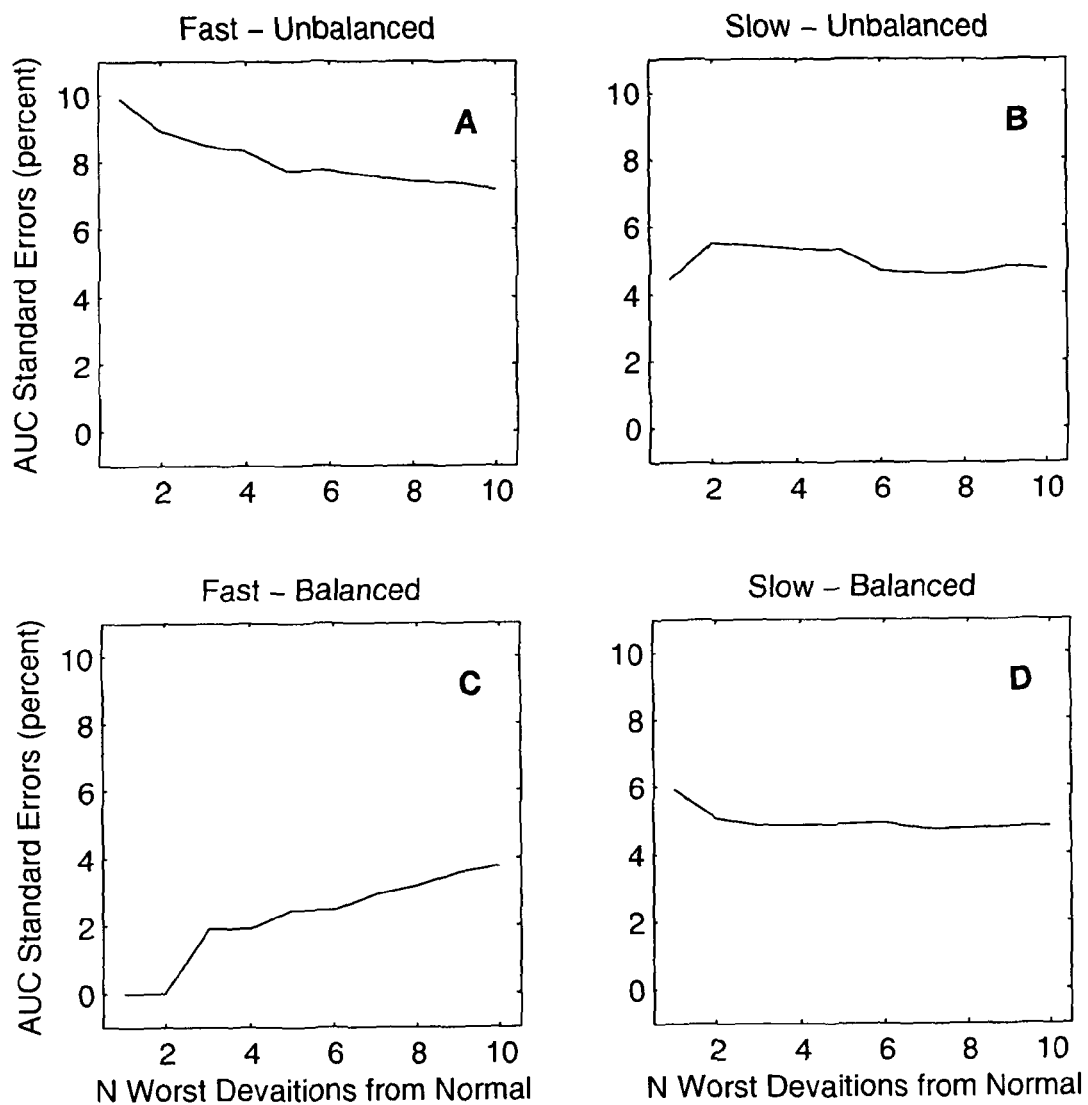
FIG. 19 shows the estimated percent standard errors in the graphs of FIG. 18. indicating the that the estimates of the AUC in FIG. 18 are good, especially the value of 100 for the balanced fast stimulus.

FIG. 18 shows plots of AUC versus N, where N varied from 1, the worst deviation, to the 10 worst deviations. The ROC plots examined data from patients from eyes with moderate to severely affected eyes, i.e. MD≥6 dB. The effect of balancing was particularly dramatic on the fast stimulus data, where percent AUC for the first few worst deviations increased from about 76% to 100%. The effects were less dramatic for the slow stimuli, the main effect being that the AUC values remained consistently higher as N increased. As can be seen from FIG. 19, which shows the estimated percent standard errors in the respective graphs of FIG. 18, the estimates of the AUC in FIG. 18 are good, especially the value of 100 for the balanced fast stimulus.

Therefore, it can be clearly seen that the balancing method, in conjunction with avoiding the very saturating part of the stimulus response function, gives significant improvement in the diagnostic efficacy, thus enhancing the ability of multifocal pupil based perimetry to detect differences from particular sets of normative data.

The methods and apparatus described herein, and/or shown in the drawings and examples, are presented by way of example only and are not limiting as to the scope of the invention. Unless otherwise specifically stated, individual aspects and components of the methods and/or apparatus may be modified, or may have been substituted therefore known equivalents, or as yet unknown substitutes such as may be developed in the future or such as may be found to be acceptable substitutes in the future. The methods and/or apparatus may also be modified for a variety of applications while remaining within the scope and spirit of the claimed invention, since the range of potential applications is great, and since it is intended that the present methods and/or apparatus be adaptable to many such variations.

What is claimed is:

1. A method for assessing the nervous system of a subject, the method comprising the steps of:
   presenting a sequence of selected individual stimuli from at least one stimulus ensemble to the nervous system of a subject adapted to evoke pupillary responses in at least one pupil of the subject, said stimulus ensemble comprising a plurality of individual stimuli, selected individual stimuli being concurrently presented in the sequence, the individual stimuli each being individually balanced such that the pupillary responses evoked by individual stimuli in the ensemble are balanced according to the strength of the neural responses evoked by the individual stimuli, the individual stimuli each being individually balanced such that responses of the pupils to more effective stimuli in the ensemble are reduced to enable larger responses of the pupils to less effective stimuli;
   detecting using a sensor responses of at least one pupil evoked by the stimuli; and
   relating the detected pupillary responses to the function of the subject's neural responses to at least two of the individual stimuli of the ensemble.

2. A method as claimed in claim 1 wherein the relationship between stimulus intensity and pupillary response size is nonlinear.

3. A method as claimed in claim 1, wherein nonlinear functions define weights for balancing the pupillary response.

4. A method as claimed in claim 1 wherein different nonlinear functions are used for each individual stimulus in the ensemble.

5. A method as claimed in 1 wherein the nonlinear stimulus/response function is a power function of the form Response=K×stimulus$^z$.

6. A method as claimed in claim 5 further comprising the steps of:
   obtaining attenuating weights that are logarithmic for each of the stimuli in the ensemble, the weights being obtained by expressing the response sizes of the stimuli in the ensemble in logarithmic form to provide linear balancing weights; and
   multiplying the linear balancing weights to the power z.

7. A method as claimed in claim 6 wherein each individual stimulus in the ensemble is associated with a unique exponent for expression of the attenuating weight for each stimulus.

8. A method as in claim 1 wherein the stimuli are visual stimuli presented to a subject at multiple locations in the visual field one or both of the subjects eyes, the resulting set of pupillary responses providing a map of visual function across the visual field of the one or both eyes.

9. A method as claimed in claim 8 wherein the ensemble of visual stimuli is a multifocal stimuli ensemble, the appearance or non-appearance of individual stimuli in the ensemble or other modulations of the stimuli such as intensity, colour (hue) or spatial frequency being controlled by statistically independent sequences.

10. A method as claimed in claim 9 wherein the statistically independent sequences are statistically independent aperiodic pseudorandom sequences.

11. A method as claimed in claim 8 wherein selected individual stimuli of the ensemble are associated with a weighting function, the luminance of the selected stimuli being controlled such that regions of the visual field in which unweighted stimuli evoke large neural responses is decreased.

12. A method as claimed in claim 8 wherein the ensemble of visual stimuli are presented as an ensemble of grating or checkerboard stimuli that are dominated by a range of different spatial frequencies for determination of the visual acuity or spatial frequency tuning of the tested portion of a subject's visual field.

13. A method as claimed in claim 12 wherein the ensemble of stimuli are presented at one or a plurality of spatially resolved locations in the visual field of the subject, such that the pupillary responses to the spatially resolved stimuli are representative of the neural responses to the concurrently presented spatial frequencies thereby to obtain information about the visual acuity and spatial frequency sensitivity of the subject.

14. A method as claimed in claim 8 wherein the visual stimuli are adapted to provide a measure of the distance to objects in the visual field, by presenting stereo disparity cues to each of the subject's eyes, such that the pupillary responses are representative of the function of the accommodative system of the subject's eyes.

15. A method as claimed in claim 8 wherein the ensemble of visual stimuli is a first ensemble for presentation to one eye of the subject, the method further comprising:
   concurrently presenting a second ensemble of unique visual stimuli to the other eye of the subject;
   recording the pupillary responses of a selected one of the two retinas;
   characterising the pupillary response of the retina associated with the recorded pupil by the direct pupil response; and
   characterising the pupillary response of the other retina by the consensual response of the recorded pupil.

16. A method as in claim 1 wherein the visual stimuli at one or several locations alternate between one of a number of stimulus conditions.

17. A method as claimed in claim 16 wherein the stimulus conditions are selected from the group consisting of stimulus luminance level, stimulus colour or hue, and wherein the stimulus conditions for each stimulus in the ensemble is each controlled by a unique statistically independent sequence such that the pupillary responses are representative of the neural responses affected by a stimulus space spanned by those stimulus conditions.

18. A method as claimed in claim 1 wherein the stimuli in the ensemble are adapted such that the pupillary responses evoked by said stimuli are substantially unsaturated.

19. A method as claimed in claim 1 wherein the ensemble of stimuli is an ensemble of auditory stimuli.

20. A method as claimed in claim 1 wherein the ensemble of stimuli evoke particular emotions, or modulate the mental health of a subject, the method comprising recording the pupillary response of the subjected evoked by the ensemble of stimuli; and characterising the function of those neural mediated emotional or mental health mechanisms of the subject from the recorded responses.

21. A method as claimed in claim 1 wherein the ensemble of stimuli is an ensemble of different drugs or other chemical substances, or difference dosages of a drug or substance, that are known to affect the function of the pupils.

22. A method as claimed in claim 1 wherein the ensemble of stimuli comprises a mixture of visual, accommodative, auditory, emotional, or chemical stimuli.

23. A method as claimed in claim 1, wherein the stimuli are controlled by statistically independent sequences with a selected mean inter-stimulus symbol interval period.

24. A method as claimed in claim 23 wherein the mean inter-stimulus interval period is selected to be in the range of about 0.25 s/region to about 16 s/region.

25. A method as claimed in claim 24 wherein the mean inter-stimulus interval period is selected to be either about 1 s/region or about 4 s/region.

26. A system for assessing the nervous system of a subject, the system comprising:
   means for generating sequences of stimuli from at least one stimulus ensemble adapted to evoke pupillary responses in at least one pupil of the subject, said stimulus ensemble comprising a plurality of individual stimuli, the stimulus generation means individually determining at least one weighting function for each of the individual stimuli in the stimulus ensemble such that the pupillary responses to individual stimuli in the ensemble are balanced according to the strength of the neural responses evoked by the individual stimuli, the individual stimuli each being individually balanced such that responses of the pupils to more effective stimuli in the ensemble are reduced to enable larger responses of the pupils to less effective stimuli;
   display means for presenting said sequence of balanced stimuli to the nervous system of a subject for the generation of pupillary responses in at least one pupil of the subject;
   a sensor for detecting the pupillary responses of at least one pupil evoked by the sequence of balanced stimuli; and
   a processor for recording and relating the detected pupillary responses to relate them to the function of the subject's neural responses to at least two of the individual stimuli of the ensemble.

27. A system as claimed in claim 26 further comprising a database of recorded data, the recorded data comprising information on at least one or more of:
   the strength or mean strength of the neural responses evoked in at least one subject by the individual stimuli;
   the strength or mean strength of the pupillary responses evoked in at least one subject by the individual stimuli;
   wherein the stimulus generation means determines the at least one weighting function for each of the individual stimuli from an analysis of the recorded data.

28. A system as claimed in claim 27 wherein the analysis of the recorded data for determination of the weighting function(s) provides a relationship between the intensity of the individual stimuli and pupillary responses evoked therefrom in the form of one or more nonlinear functions.

29. A system as claimed in claim 28 wherein the nonlinear stimulus/response function is a power function of the form Response=K×stimulus$^z$.

30. A system as claimed in claim 29 wherein each individual stimulus in the ensemble is associated with a unique exponent for expression of the attenuating weight for each stimulus.

31. A system as claimed in claim 26 wherein the stimuli are visual stimuli presented to a subject at multiple locations in the visual field one or both of the subject's eyes, the resulting set of pupillary responses providing a map of visual function across the visual field of the one or both eyes.

32. A system as claimed in claim 26, wherein the means for generating sequences of stimuli is adapted to present the statistically independent sequences of stimuli with a selected mean inter-stimulus symbol interval period.

33. A system as claimed in claim 32 wherein the means for generating sequences of stimuli is adapted to selectively present the statistically independent sequences of stimuli with a mean inter-stimulus interval period wherein the mean inter-stimulus interval period is selected to be in the range of about 0.25 s/region to about 16 s/region.

34. A system as claimed in claim 33 wherein the mean inter-stimulus interval period is selected to be either about 1 s/region or about 4 s/region.

35. A system as claimed in claim 32 wherein the statistically independent sequences are statistically independent aperiodic pseudorandom sequences.

* * * * *